United States Patent
Yao et al.

(10) Patent No.: US 11,911,201 B2
(45) Date of Patent: Feb. 27, 2024

(54) SYSTEMS AND METHODS FOR DETERMINING POSITION OF REGION OF INTEREST

(71) Applicant: SHANGHAI UNITED IMAGING HEALTHCARE CO., LTD., Shanghai (CN)

(72) Inventors: Feng Yao, Shanghai (CN); Jia Zhao, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 396 days.

(21) Appl. No.: 17/136,071

(22) Filed: Dec. 29, 2020

(65) Prior Publication Data

US 2021/0259654 A1    Aug. 26, 2021

(30) Foreign Application Priority Data

Feb. 21, 2020   (CN) .......................... 202010107908.8

(51) Int. Cl.
*A61B 6/00* (2006.01)
*G06N 3/08* (2023.01)
*G16H 30/40* (2018.01)

(52) U.S. Cl.
CPC .............. *A61B 6/469* (2013.01); *A61B 6/481* (2013.01); *A61B 6/488* (2013.01); *A61B 6/5217* (2013.01); *G06N 3/08* (2013.01); *G16H 30/40* (2018.01)

(58) Field of Classification Search
CPC ......... A61B 6/469; A61B 6/481; A61B 6/488; A61B 6/5217; G16H 30/40; G06N 3/08; G06T 7/0012; G06T 2207/10072; G06T 2207/10116; G06T 2207/20081; G06T 2207/20104; G06T 7/246; G06F 18/214; G06V 10/25

See application file for complete search history.

(56) References Cited

U.S. PATENT DOCUMENTS

| | | | |
|---|---|---|---|
| 2006/0178836 A1* | 8/2006 | Bai | G16Z 99/00 |
| | | | 702/19 |
| 2008/0294049 A1* | 11/2008 | Guracar | G06T 7/0016 |
| | | | 600/458 |
| 2009/0022265 A1 | 1/2009 | Takase et al. | |

(Continued)

FOREIGN PATENT DOCUMENTS

| | | | | |
|---|---|---|---|---|
| CN | 108514425 A | * | 9/2018 | ............. A61B 6/032 |
| CN | 108514425 A | | 9/2018 | |

(Continued)

OTHER PUBLICATIONS

The Extended European Search Report in European Application No. 20217438.9 dated Jun. 2, 2021, 7 pages.

*Primary Examiner* — Siamak Harandi
(74) *Attorney, Agent, or Firm* — METIS IP LLC

(57) ABSTRACT

The present disclosure relates to systems and methods for positioning a region of interest (ROI). The systems may obtain an image of an object captured by an imaging device. The systems may extract image information of the image. The systems may obtain feature information of a region of interest (ROI) in the object. The systems may determine position information of the ROI in the image using a positioning model based on the image information of the image and the feature information of the ROI.

18 Claims, 10 Drawing Sheets

(56) References Cited

U.S. PATENT DOCUMENTS

| | | | |
|---|---|---|---|
| 2010/0249582 A1* | 9/2010 | Feuerlein | A61B 6/481 |
| | | | 600/431 |
| 2010/0292570 A1 | 11/2010 | Tsukagoshi | |
| 2011/0144495 A1* | 6/2011 | Wilkening | A61B 8/483 |
| | | | 600/443 |
| 2013/0116565 A1* | 5/2013 | Miyama | A61B 8/5276 |
| | | | 600/443 |
| 2014/0016868 A1* | 1/2014 | Xuan | A61B 6/469 |
| | | | 382/191 |
| 2015/0310638 A1 | 10/2015 | Jia et al. | |
| 2016/0022238 A1* | 1/2016 | Park | A61B 6/5217 |
| | | | 600/407 |
| 2017/0186158 A1* | 6/2017 | Goto | G01R 33/5601 |
| 2018/0315183 A1* | 11/2018 | Milioni De Carvalho | |
| | | | G16H 20/10 |
| 2019/0117182 A1* | 4/2019 | Li | A61B 6/54 |
| 2020/0234446 A1* | 7/2020 | Mischi | G16H 50/50 |

FOREIGN PATENT DOCUMENTS

| | | |
|---|---|---|
| CN | 110070083 A | 7/2019 |
| JP | 2008000499 A | 1/2008 |

* cited by examiner

SYSTEMS AND METHODS FOR DETERMINING POSITION OF REGION OF INTEREST

CROSS-REFERENCE TO RELATED APPLICATIONS

This application claims priority to Chinese Patent Application No. 202010107908.8 filed on Feb. 21, 2020, the contents of which are incorporated herein by reference.

TECHNICAL FIELD

The present disclosure generally relates to image processing technology, and more particularly, relates to systems and methods for positioning a region of interest (ROI).

BACKGROUND

Medical imaging technology, such as contrast agent tracking technology is widely used in disease diagnosis and/or treatment for various medical conditions (e.g., tumors, coronary heart diseases, or brain diseases). Taking the contrast agent tracking technology as an example, a locator scan may be performed on an object (e.g., a patient) to determine a position of an ROI (e.g., a lesion), and then one or more tracker scans may be performed sequentially to monitor a concentration of the contrast agent in the ROI. Conventionally, a user (e.g., a doctor) may mark the ROI on a locator image of the object obtained by the locator scan and record the position of the ROI. Further, under a premise that the position of the ROI remains unchanged, subsequent tracker scans are performed. However, in fact, due to factors such as a rigid motion of the object, respiratory motion of the object, etc., the position of the ROI may change after the locator scan. The inaccurate ROI position may decrease the accuracy of the concentration monitoring of the contrast agent. Therefore, it is desirable to provide systems and methods for dynamic ROI positioning, thereby improving the accuracy of the positioning of the ROI and subsequence procedures.

SUMMARY

An aspect of the present disclosure relates to a system for positioning a region of interest (ROI). The system may include at least one storage device including a set of instructions and at least one processor in communication with the at least one storage device. When executing the set of instructions, the at least one processor may be directed to cause the system to implement operations. The operations may include obtain an image of an object captured by an imaging device; extracting image information of the image; obtaining feature information of a region of interest (ROI) in the object; and determining position information of the ROI in the image using a positioning model based on the image information of the image and the feature information of the ROI.

In some embodiments, the obtaining feature information of an ROI in the object may include obtaining an initial image of the object by performing a preliminary scan on the object; obtaining marking information of the ROI from the initial image of the object; and obtaining the feature information of the ROI. The marking information may include a size of the ROI, a shape of the ROI, and/or a position of the ROI in the initial image.

In some embodiments, the image of the object may be obtained by performing, on the object, each of one or more tracker scans that are sequentially performed to monitor a concentration of a contrast agent in the ROI.

In some embodiments, the image information may include pixel values of pixels or voxel values of voxels in the image. The feature information of the ROI may includes a size of the ROI, a shape of the ROI; an anatomical feature of the ROI, imaging parameter information associated with the ROI, and/or pixel information associated with the ROI.

In some embodiments, the imaging parameter information associated with the ROI may include CT values of the ROI, an average CT value of the ROI, a variance of the CT values of the ROI, and/or a contrast of the ROI in a subtraction image of the image.

In some embodiments, the operations may further include updating the imaging parameter information associated with the ROI based on the position information of the ROI in the image; determining whether the updated imaging parameter information associated with the ROI satisfies a condition relating to a concentration of a contrast agent; and performing imaging operations based on a determination result of whether the imaging parameter information associated with the ROI satisfies the condition.

In some embodiments, the determination result may include that the updated imaging parameter information associated with the ROI satisfies the condition. The imaging operations may include obtaining a second image of the object captured by the imaging device at a second time point subsequent to a first time point when the image is acquired; identifying the ROI in the second image using the positioning model based on image information of the second image and feature information of the ROI in the second image; and determining whether updated imaging parameter information associated with the ROI in the second image satisfies the condition.

In some embodiments, the determination result may include that the updated imaging parameter information associated with the ROI does not satisfy the condition. The imaging operations may include performing a medical procedure on the object.

In some embodiments, the operations may further include determining a curve indicating a change of the updated imaging parameter information associated with the ROI corresponding to a plurality of images acquired at different time points and transmitting the curve to a terminal device for displaying.

In some embodiments, the determining position information of the ROI in the image by using a positioning model based on the image information of the image and the feature information of the ROI may include inputting the image information of the image and the feature information of the ROI into the positioning model and determining the position information of the ROI in the image based on an output of the positioning model.

In some embodiments, the positioning model may be obtained by a training process. The training process may include obtaining a plurality of training samples and obtaining the positioning model by training a preliminary positioning model based on the plurality of training samples. Each of the plurality of training samples may include a sample image, image information of the sample image, an ROI in the sample image, feature information of the ROI in the sample image, and reference position information of the ROI in the sample image.

In some embodiments, the positioning model may include a machine learning model or a regression model.

A further aspect of the present disclosure relates to a method for positioning a region of interest (ROI). The method may be implemented on a computing device including at least one processor and at least one storage device. The method may include obtaining an image of an object captured by an imaging device; extracting image information of the image; obtaining feature information of a region of interest (ROI) in the object; and determining position information of the ROI in the image using a positioning model based on the image information of the image and the feature information of the ROI.

A still further aspect of the present disclosure relates to a non-transitory computer readable medium including executable instructions. When the executable instructions are executed by at least one processor, the executable instructions may direct the at least one processor to perform a method. The method may include obtaining an image of an object captured by an imaging device; extracting image information of the image; obtaining feature information of a region of interest (ROI) in the object; and determining position information of the ROI in the image using a positioning model based on the image information of the image and the feature information of the ROI.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

Figure 1:
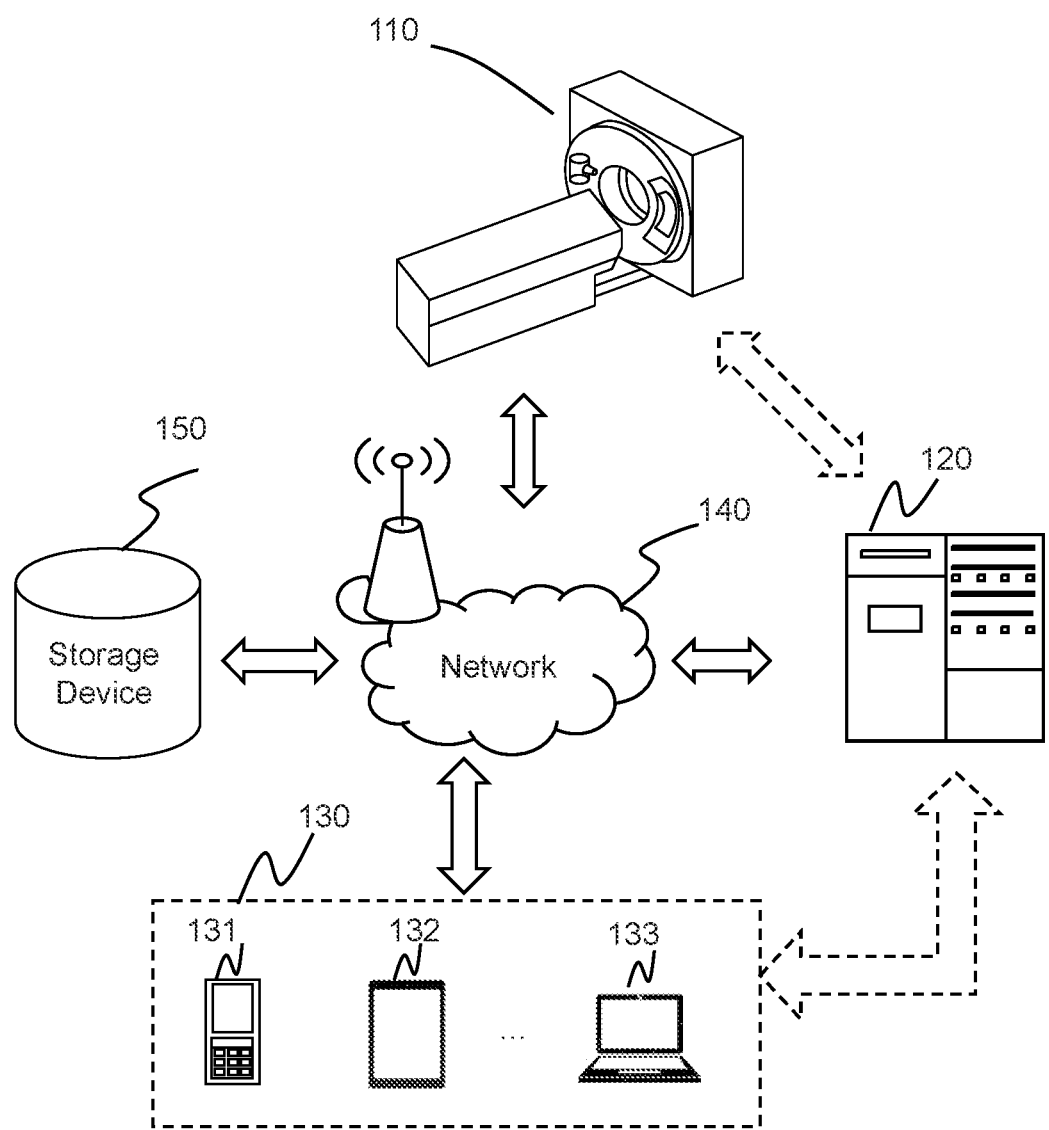
FIG. 1 is a schematic diagram illustrating an exemplary medical system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is to describe particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the terms "system," "unit," "module," and/or "block" used herein are one method to distinguish different components, elements, parts, sections, or assemblies of different levels in ascending order. However, the terms may be displaced by another expression if they achieve the same purpose.

Generally, the words "module," "unit," or "block," as used herein, refer to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 illustrated in FIG. 2 and/or the central processing unit (CPU) 340 illustrated FIG. 3) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may apply to a system, an engine, or a portion thereof.

It will be understood that when a unit, engine, module, or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood, the operations of the flowcharts may be implemented not in order. Conversely, the operations may be implemented in inverted order, or simultaneously. Moreover, one or more other operations may be added to the flowcharts. One or more operations may be removed from the flowcharts.

Provided herein are systems and methods for non-invasive biomedical imaging/treatment, such as for disease diagnostic, disease therapy, or research purposes. In some embodiments, the systems may include an imaging system. The imaging system may include a single modality system and/or a multi-modality system. The term "modality" used herein broadly refers to an imaging or treatment method or technology that gathers, generates, processes, and/or analyzes imaging information of a subject or treatments the subject. The single modality system may include, for example, an ultrasound imaging system, an X-ray imaging system, a computed tomography (CT) system, a magnetic resonance imaging (MRI) system, an ultrasonography system, a positron emission tomography (PET) system, an optical coherence tomography (OCT) imaging system, an ultrasound (US) imaging system, an intravascular ultrasound (IVUS) imaging system, a near-infrared spectroscopy (NIRS) imaging system, or the like, or any combination thereof. The multi-modality system may include, for example, an X-ray imaging-magnetic resonance imaging (X-ray-MRI) system, a positron emission tomography-X-ray imaging (PET-X-ray) system, a single-photon emission computed tomography-magnetic resonance imaging (SPECT-MRI) system, a positron emission tomography-computed tomography (PET-CT) system, a C-arm system, a positron emission tomography-magnetic resonance imaging (PET-MR) system, a digital subtraction angiography-magnetic resonance imaging (DSA-MRI) system, etc. In some embodiments, the medical system may include a treatment system. The treatment system may include a treatment plan system (TPS), image-guided radiotherapy (IGRT), etc. It should be noted that the medical system described below is merely provided for illustration purposes, and not intended to limit the scope of the present disclosure.

An aspect of the present disclosure relates to systems and methods for ROI positioning. The systems may obtain an image (e.g., a tracker image obtained during each tracker scan) of an object (e.g., a patient) captured by an imaging device and extract image information (e.g., pixel values of pixels in the image) of the image. Further, the systems may obtain feature information (e.g., a size of the ROI, a shape of the ROI, an anatomical feature of the ROI, imaging parameter information associated with the ROI, pixel information associated with the ROI) of an ROI (e.g., a lesion) in the object. According to the image information of the image and the feature information of the ROI, the systems may determine position information of the ROI in the image using a positioning model (e.g., a machine learning model, a regression model).

According to the systems and methods of the present disclosure, after a scan (e.g., tracker scan) is performed, a position of the ROI may be determined via the positioning model, instead of assuming that the position of the ROI remains unchanged during one or more tracker scans, which can improve the accuracy of the positioning of the ROI, thereby improving the accuracy of ROI monitoring (e.g., concentration monitoring of a contrast agent) based on the position of the ROI.

FIG. 1 is a schematic diagram illustrating an exemplary medical system according to some embodiments of the present disclosure. As illustrated, the medical system 100 may include an imaging device 110, a processing device 120, a terminal device 130, a network 140, and a storage device 150. The components of the medical system 100 may be connected in one or more of various ways. Mere by way of example, as illustrated in FIG. 1, the imaging device 110 may be connected to the processing device 120 through the network 140. As another example, the imaging device 110 may be connected to the processing device 120 directly (as indicated by the bi-directional arrow in dotted lines linking the imaging device 110 and the processing device 120). As a further example, the storage device 150 may be connected to the processing device 120 directly or through the network 140. As still a further example, the terminal device 130 may be connected to the processing device 120 directly (as indicated by the bi-directional arrow in dotted lines linking the terminal device 130 and the processing device 120) or through the network 140.

The imaging device 110 may be configured to acquire imaging data relating to at least one part of a subject. The imaging device 110 may scan the subject or a portion thereof that is located within its detection region and generate imaging data relating to the subject or the portion thereof. The imaging data relating to at least one part of a subject may include an image (e.g., an image slice), projection data, or a combination thereof. In some embodiments, the imaging data may be two-dimensional (2D) imaging data, three-dimensional (3D) imaging data, four-dimensional (4D) imaging data, or the like, or any combination thereof. In some embodiments, the imaging device 110 may include a single modality imaging device. For example, the imaging device 110 may include a digital subtraction angiography (DSA), a positron emission tomography (PET) device, a single-photon emission computed tomography (SPECT) device, a magnetic resonance imaging (MRI) device (also referred to as an MR device, an MR scanner), a computed tomography (CT) device, an ultrasonography scanner, a digital radiography (DR) scanner, or the like, or any combination thereof. In some embodiments, the imaging device 110 may include a multi-modality imaging device. Exemplary multi-modality imaging devices may include a PET-CT device, a PET-MR device, or the like, or a combination thereof.

The processing device 120 may process data and/or information obtained from the imaging device 110, the terminal device 130, and/or the storage device 150. For example, the processing device 120 may obtain an image of an object captured by the imaging device 110 and extract image information of the image. Further, the processing device 120 may obtain feature information of an ROI in the object. According to the image information of the image and the feature information of the ROI, the processing device 120 may determine position information of the ROI in the image using a positioning model. In some embodiments, the processing device 120 may include a central processing unit (CPU), a digital signal processor (DSP), a system on a chip (SoC), a microcontroller unit (MCU), or the like, or any combination thereof. In some embodiments, the processing device 120 may include a computer, a user console, a single server or a server group, etc. The server group may be centralized or distributed. In some embodiments, the processing device 120 may be local or remote. For example, the processing device 120 may access information and/or data stored in the imaging device 110, the terminal device 130, and/or the storage device 150 via the network 140. As another example, the processing device 120 may be directly connected to the imaging device 110, the terminal device 130, and/or the storage device 150 to access stored information and/or data. In some embodiments, the processing device 120 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 120 or a portion of the processing device 120 may be integrated into the imaging device 110. In some embodiments, the processing device 120 may be implemented by a computing device 200 including one or more components as described in FIG. 2.

The terminal device 130 may include a mobile device 131, a tablet computer 132, a laptop computer 133, or the like, or any combination thereof. In some embodiments, the mobile device 131 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the smart mobile device may include a mobile phone, a personal digital assistant (PDA), a gaming device, a navigation device, a point of sale (POS) device, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal device 130 may be part of the processing device 120.

The network 140 may include any suitable network that can facilitate the exchange of information and/or data for the medical system 100. In some embodiments, one or more components (e.g., the imaging device 110, the processing device 120, the storage device 150, the terminal device 130) of the medical system 100 may communicate information and/or data with one or more other components of the medical system 100 via the network 140. For example, the processing device 120 may obtain data (e.g., the image of the object) from the imaging device 110 via the network 140. As another example, the terminal device 130 may receive the position information of the ROI from the processing device 120 via the network 140. In some embodiments, one or more components (e.g., the imaging device 110, the processing device 120, the storage device 150, the terminal device 130) of the medical system 100 may communicate information and/or data with one or more external resources such as an external storage device of a third party, etc. For example, the processing device 120 may obtain a positioning model from a database of a vendor or manufacture (e.g., a manufacture of the imaging device 110) that provides and/or updates the positioning model. The network 140 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 140 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 140 may include one or more network access points. For example, the network 140 may include wired and/or wireless network access points, such as base stations and/or Internet exchange points, through which one or more components of the medical system 100 may be connected to the network 140 to exchange data and/or information.

The storage device 150 may store data, instructions, and/or any other information. In some embodiments, the storage device 150 may store data obtained from the imaging device 110, the terminal device 130, and/or the processing device 120. In some embodiments, the storage device 150 may store data and/or instructions that the processing device 120 may execute or use to perform exemplary methods described in the present disclosure. In some embodiments, the storage device 150 may include a mass storage device, a removable storage device, a volatile read-and-write memory, a read-only memory (ROM), or the like, or a combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), a digital versatile disk ROM, etc. In some embodiments, the storage device 150 may be implemented on a cloud platform as described elsewhere in the disclosure.

In some embodiments, the storage device 150 may be connected to the network 140 to communicate with one or more components (e.g., the imaging device 110, the processing device 120, the terminal device 130) of the medical system 100. One or more components of the medical system 100 may access the data or instructions stored in the storage device 150 via the network 140. In some embodiments, the storage device 150 may be directly connected to or communicate with one or more components of the medical system 100. In some embodiments, the storage device 150 may be part of the processing device 120 or the terminal device 130.

Figure 2:
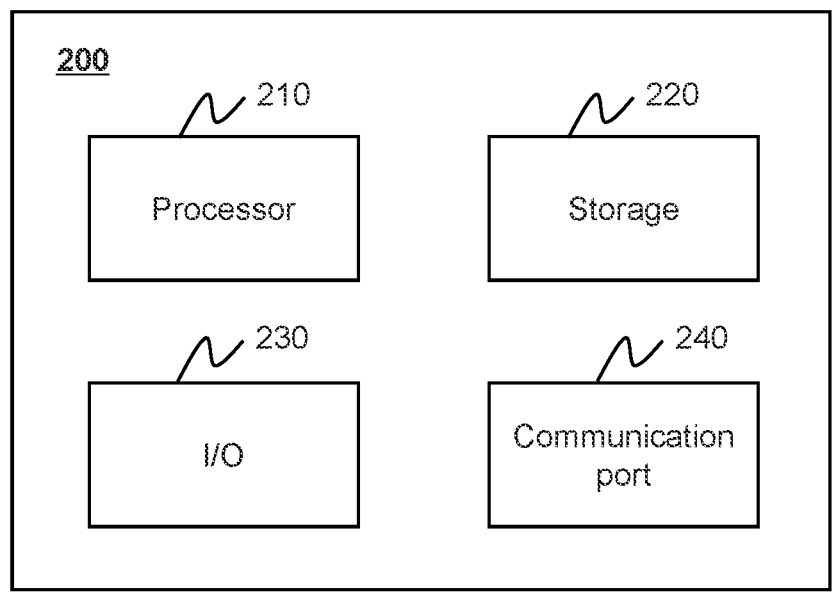
FIG. 2 is a schematic diagram illustrating exemplary hardware and/or software components of an exemplary computing device according to some embodiments of the present disclosure.

It should be noted that the above description of the medical system 100 is merely provided for the purposes of illustration, and not intended to limit the scope of the present disclosure. For persons having ordinary skills in the art, multiple variations and modifications may be made under the teachings of the present disclosure. For example, the medical system 100 may include one or more additional components and/or one or more components of the medical system 100 described above may be omitted. Additionally or alternatively, two or more components of the medical system 100 may be integrated into a single component. A component of the medical system 100 may be implemented on two or more sub-components, FIG. 2 is a schematic diagram illustrating exemplary hardware and/or software components of an exemplary computing device according to some embodiments of the present disclosure. The computing device 200 may be used to implement any component of the medical system 100 as described herein. For example, the processing device 120 and/or the terminal device 130 may be implemented on the computing device 200, respectively, via its hardware, software program, firmware, or a combination thereof. Although only one such computing device is shown, for convenience, the computer functions relating to the medical system 100 as described herein may be implemented in a distributed fashion on a number of similar platforms, to distribute the processing load. As illustrated in FIG. 2, the computing device 200 may include a processor 210, a storage 220, an input/output (I/O) 230, and a communication port 240.

The processor 210 may execute computer instructions (e.g., program codes) and perform functions of the processing device 120 in accordance with techniques described herein. The computer instructions may include, for example, routines, programs, objects, components, data structures, procedures, modules, and functions, which perform particular functions described herein. For example, the processor 210 may process data obtained from the imaging device 110, the storage device 150, the terminal device 130, and/or any other components of the medical system 100.

In some embodiments, the processor 210 may include one or more hardware processors, such as a microcontroller, a microprocessor, a reduced instruction set computer (RISC), an application-specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field-programmable gate array (FPGA), an advanced RISC machine (ARM), a programmable logic device (PLD), any circuit or processor capable of executing one or more functions, or the like, or a combination thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the imaging device 110, the storage device 150, the terminal device 130, and/or any other component of the medical system 100. In some embodiments, the storage 220 may include a mass storage device, a removable storage device, a volatile read-and-write memory, a read-only memory (ROM), or the like, or a combination thereof. In some embodiments, the storage 220 may store one or more programs and/or instructions to perform exemplary methods described in the present disclosure. For example, the storage 220 may store a program for the processing device 120 to execute to determine a positioning model. As another example, the storage 220 may store a program for the processing device 120 to execute to apply the positioning model to determine the position information of the ROI.

The I/O 230 may input and/or output signals, data, information, etc. In some embodiments, the I/O 230 may enable a user interaction with the processing device 120. In some embodiments, the I/O 230 may include an input device and an output device. The input device may include alphanumeric and other keys that may be input via a keyboard, a touch screen (for example, with haptics or tactile feedback), a speech input, an eye-tracking input, a brain monitoring system, or any other comparable input mechanism. The input information received through the input device may be transmitted to another component (e.g., the processing device 120) via, for example, a bus, for further processing. Other types of the input device may include a cursor control device, such as a mouse, a trackball, or cursor direction keys, etc. The output device may include a display (e.g., a liquid crystal display (LCD), a light-emitting diode (LED)-based display, a flat panel display, a curved screen, a television device, a cathode ray tube (CRT), a touch screen), a speaker, a printer, or the like, or a combination thereof.

The communication port 240 may be connected to a network (e.g., the network 140) to facilitate data communications. The communication port 240 may establish connections between the processing device 120 and one or more components (e.g., the imaging device 110, the storage device 150, and/or the terminal device 130) of the medical system 100. The connection may be a wired connection, a wireless connection, any other communication connection that can enable data transmission and/or reception, and/or a combination of these connections. The wired connection may include, for example, an electrical cable, an optical cable, a telephone wire, or the like, or a combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
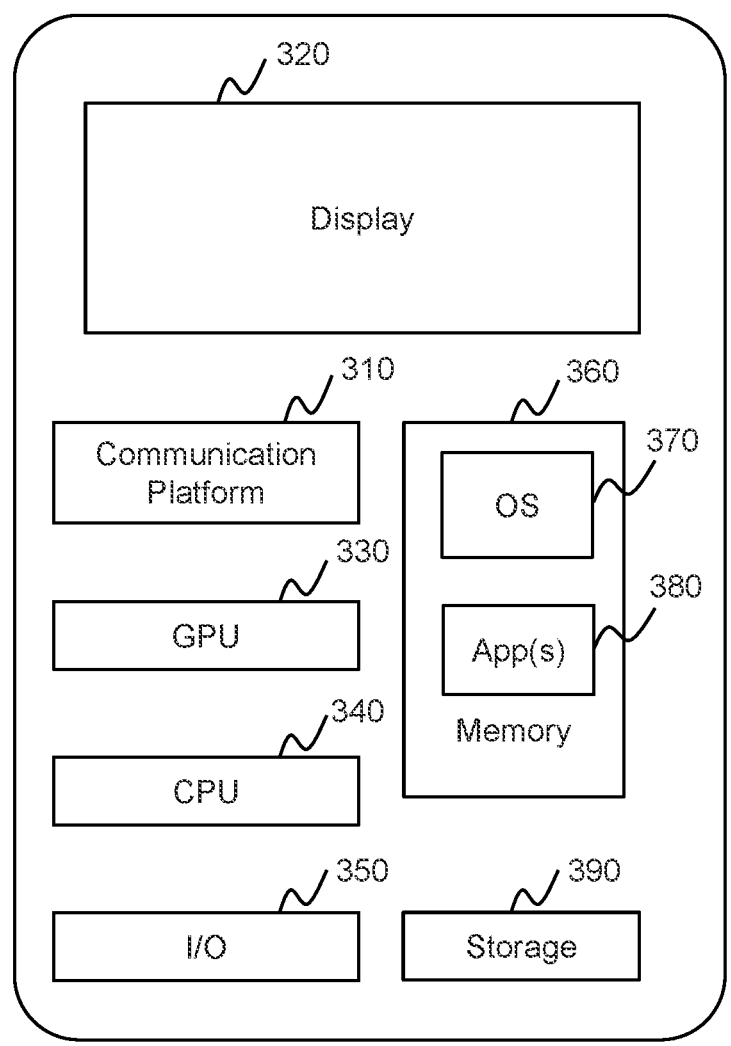
FIG. 3 is a schematic diagram illustrating exemplary hardware and/or software components of an exemplary mobile device according to some embodiments of the present disclosure.

FIG. 3 is a schematic diagram illustrating exemplary hardware and/or software components of an exemplary mobile device according to some embodiments of the present disclosure. In some embodiments, one or more components (e.g., the terminal device 130, the processing device 120) of the medical system 100 may be implemented on one or more components of the mobile device 300.

As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™, etc.) and one or more applications 380 may be loaded into the memory 360 from the storage 390 in order to be executed by the CPU 340, The applications 380 may include a browser or any other suitable mobile apps for receiving and rendering information relating to the medical system 100. User interactions with the information stream may be achieved via the I/O 350 and provided to the processing device 120 and/or other components of the medical system 100 via the network 140.

To implement various modules, units, and their functionalities described in the present disclosure, computer hardware platforms may be used as the hardware platform(s) for one or more of the elements described herein. The hardware elements, operating systems, and programming languages of such computers are conventional in nature, and it is presumed that those skilled in the art are adequately familiar therewith to adapt those technologies to generate an image as described herein. A computer with user interface elements may be used to implement a personal computer (PC) or another type of work station or terminal device, although a computer may also act as a server if appropriately programmed. It is believed that those skilled in the art are familiar with the structure, programming, and general operation of such computer equipment and as a result, the drawings should be self-explanatory.

Figure 4:
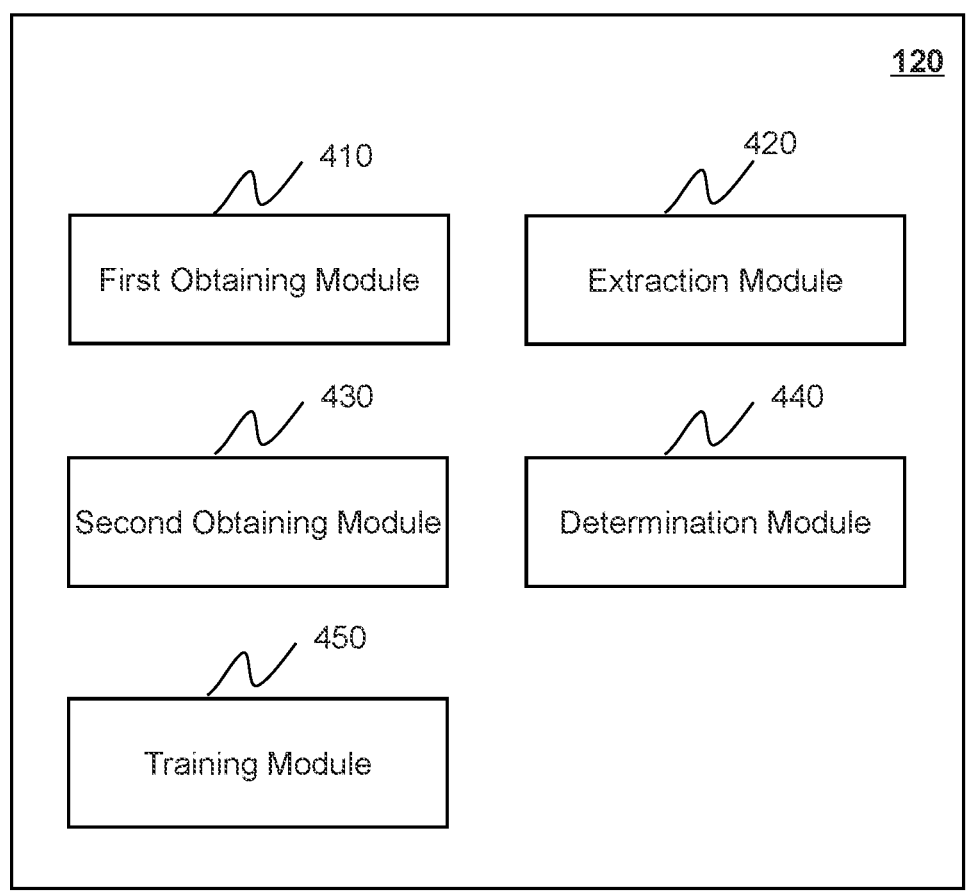
FIG. 4 is a block diagram illustrating an exemplary processing device according to some embodiments of the present disclosure.

FIG. 4 is a block diagram illustrating an exemplary processing device according to some embodiments of the present disclosure. The processing device 120 may be implemented on the computing device 200 (e.g., the processor 210) illustrated in FIG. 2 or the mobile device 300 illustrated in FIG. 3. The processing device 120 may include a first obtaining module 410, an extraction module 420, a second obtaining module 430, a determination module 440, and a training module 450.

The first obtaining module 410 may be configured to obtain an image of an object captured by an imaging device (e.g., the imaging device 110). More descriptions regarding the obtaining of the image of the object may be found elsewhere in the present disclosure. See, e.g., operation 510 in FIG. 5 and relevant descriptions thereof.

The extraction module 420 may be configured to extract image information of the image. More descriptions regarding the extraction of the image information of the image may be found elsewhere in the present disclosure. See, e.g., operation 520 in FIG. 5 and relevant descriptions thereof.

The second obtaining module 430 may be configured to obtain feature information of the region of interest (ROI) in the object. More descriptions regarding the obtaining of the feature information of the ROI may be found elsewhere in the present disclosure. See, e.g., operation 530 in FIG. 5 and relevant descriptions thereof.

The determination module 440 may be configured to determine position information of the ROI in the image using a positioning model based on the image information of the image and the feature information of the ROI. More descriptions regarding the determination of the position information of the ROI in the image may be found elsewhere in the present disclosure. See, e.g., operation 540 in FIG. 5 and relevant descriptions thereof.

In some embodiments, the determination module 440 may be configured to update imaging parameter information associated with an ROI based on the position information of the ROI in the image. Further, the determination module 440 may be configured to determine whether updated imaging parameter information associated with the ROI satisfies a condition relating to a concentration of a contrast agent. In response to determining that the updated imaging parameter information associated with the ROI satisfies the condition, the determination module 440 may obtain a second image of the object using imaging data acquired by the imaging device (e.g., the imaging device 110) at a second time point subsequent to a first time point when imaging data corresponding to the image is acquired, and identify the ROI in the second image using the positioning model based on image information of the second image and feature information of the ROI in the second image. In response to determining that the updated imaging parameter information associated with the ROI does not satisfy the condition, the determination module 440 may perform a medical procedure on the object. More descriptions regarding operations in above embodiments may be found elsewhere in the present disclosure. See, e.g., FIG. 6 and relevant descriptions thereof.

The training module 450 may be configured to obtain the positioning model by a training process. For example, the training module 450 may obtain a plurality of training samples and obtain the positioning model by training a preliminary positioning model based on the plurality of training samples. More descriptions regarding the training process may be found elsewhere in the present disclosure. See, e.g., FIG. 7 and relevant descriptions thereof.

The modules in the processing device 120 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof.

It should be noted that the above description regarding the processing device 120 is merely provided for the purposes of illustration, and not intended to limit the scope of the present disclosure. For persons having ordinary skills in the art, multiple variations and modifications may be made under the teachings of the present disclosure. In some embodiments, two or more of the modules may be combined into a single module, and any one of the modules may be divided into two or more units. For example, the first obtaining module 410 and the second obtaining module 430 may be combined as a single module which may both obtain the image of the object and the feature information of the ROI. As another example, the determination module 440 may be divided into a first determination unit configured to determine the position information of the ROI and a second determination unit configured to determine whether the imaging parameter information associated with the ROI satisfies a condition. In some embodiments, the processing device 120 may include one or more additional modules. For example, the processing device 120 may also include a transmission module (not shown) configured to transmit signals (e.g., electrical signals, electromagnetic signals) to one or more components (e.g., the imaging device 110, the terminal device 130, the storage device 150) of the medical system 100. As another example, the processing device 120 may include a storage module (not shown) used to store information and/or data (e.g., the image of the object, the image information of the image, the feature information of the ROI, the position information of the ROI) associated with the ROI positioning. In some embodiments, the training module 450 may be implemented on a separate device (e.g., a processing device independent from the processing device 120). In some embodiments, the training module 450 may be unnecessary and the positioning model may be obtained from a storage device (e.g., the storage device 150, an external storage device) disclosed elsewhere in the present disclosure. However, those variations and modifications do not depart from the scope of the present disclosure.

Figure 5:
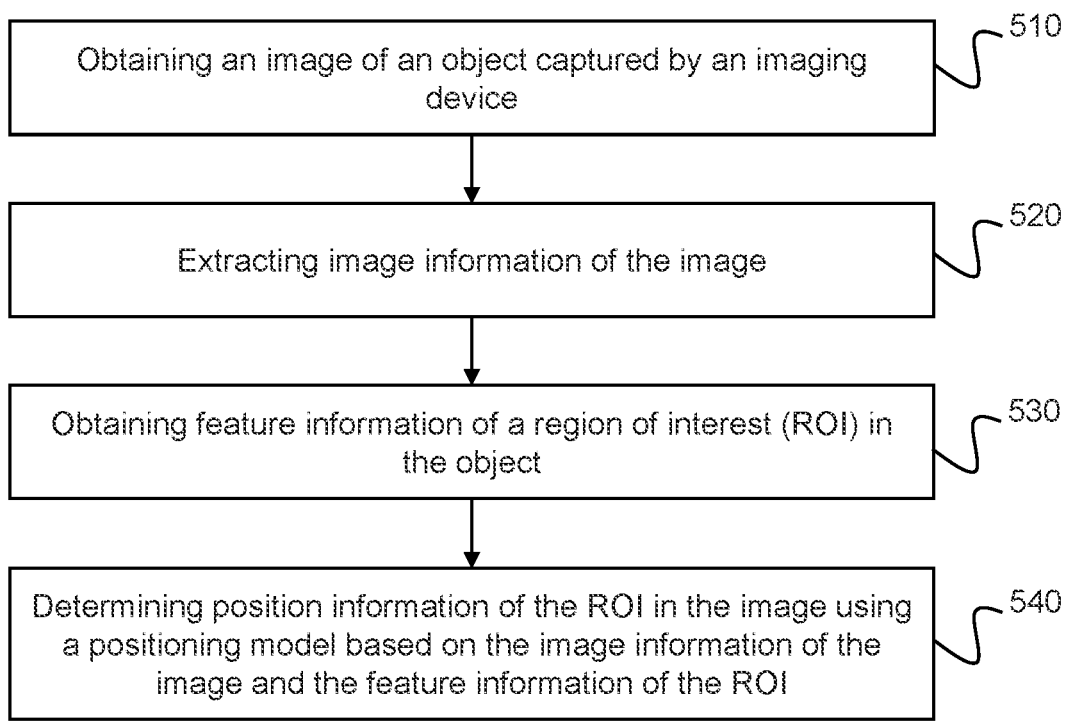
FIG. 5 is a flowchart illustrating an exemplary process for ROI positioning according to some embodiments of the present disclosure.

FIG. 5 is a flowchart illustrating an exemplary process for ROI positioning according to some embodiments of the present disclosure. In some embodiments, process 500 may be executed by the medical system 100. For example, the process 500 may be implemented as a set of instructions (e.g., an application) stored in a storage device (e.g., the storage device 150, the storage 220, and/or the storage 390). In some embodiments, the processing device 120 (e.g., the processor 210 of the computing device 200, the CPU 340 of the mobile device 300, and/or one or more modules illustrated in FIG. 4) and/or an ROI processing device 1000 (e.g., one or more modules illustrated in FIG. 10) may execute the set of instructions and may accordingly be directed to perform the process 500. The operations of the illustrated process presented below are intended to be illustrative. In some embodiments, the process 500 may be accomplished with one or more additional operations not described and/or without one or more of the operations discussed. Additionally, the order of the operations of process 500 illustrated in FIG. 5 and described below is not intended to be limiting.

In 510, the processing device 120 (e.g., the first obtaining module 410) (e.g., the interface circuit(s) of the processor 210) may obtain an image of an object captured by an imaging device (e.g., the imaging device 110).

In some embodiments, the object may include a biological object and/or a non-biological object. The biological object may be a human being (e.g., a patient), an animal, a plant, or a specific portion, organ, and/or tissue thereof. For example, the object may include the head, the neck, the thorax, the heart, the stomach, a blood vessel, a soft tissue, a tumor, a nodule, or the like, or any combination thereof, of a patient. In some embodiments, the object may be a man-made composition of organic and/or inorganic matters that are with or without life. In the present disclosure, the term "object" or "subject" are used interchangeably in the present disclosure.

In the present disclosure, a representation of an object (e.g., a patient, a subject, or a portion thereof) in an image may be referred to as "object" for brevity. For instance, a representation of an organ or tissue (e.g., a heart, a liver, a lung) in an image may be referred to as an organ or tissue for brevity. Further, an image including a representation of an object may be referred to as an image of an object or an image including an object for brevity. Still further, an operation performed on a representation of an object in an image may be referred to as an operation performed on an object for brevity. For instance, a segmentation of a portion of an image including a representation of an organ or tissue from the image may be referred to as a segmentation of an organ or tissue for brevity.

As described in connection with FIG. 1, the image of the object may include a CT image, a PET image, an X-ray image, an MR image, or the like, or any combination thereof.

In some embodiments, the processing device 120 may direct the imaging device 110 to perform a scan (e.g., a CT scan) on an object (e.g., a patient) and generate the image based on scanning data obtained from the imaging device 110. Merely by way of example, the processing device 120 may generate the image based on the scanning data according to a reconstruction algorithm (e.g., a Filter Back Projection (FBP) algorithm). In some embodiments, the image may be previously generated and stored in a storage device (e.g., the storage device 150, the storage 220, and/or the storage 390). The processing device 120 may obtain the image from the storage device via a network (e.g., the network 140).

A contrast agent tracking scan (also referred to as bolus tracking) may include a locator scan that is used to determine an initial region of interest (ROI) in the object and one or more tracker scans that are sequentially performed to monitor a concentration of a contrast agent in the ROI. Each of the locator scan and the one or more tracker scans may include a CT scan, a PET scan, an X-ray scan, a magnetic resonance (MR) scan, or the like, or any combination thereof. The processing device 120 may obtain the image of the object by performing each of the one or more tracker scans on the object. For example, the processing device 120 may direct the imaging device 110 to perform a tracker scan on the object at a first time point to obtain an image of the object. Further, the processing device 120 may direct the imaging device 110 to perform a next tracker scan on the object at a second time point subsequent to the first time point to obtain a second image of the object. The processing device 120 may monitor the concentration change of the contrast agent based on one or more images (e.g., the image obtained at the first time point, the second image obtained a second time point) obtained during the one or more tracker scans. In some embodiments, the contrast agent may be used to enhance the contrast of a structure or fluid within the object relative to the surroundings of the structure or fluid in an image. Exemplary contrast agents may include an iodine-based compound, a barium-sulfate compound, etc.

In 520, the processing device 120 (e.g., the extraction module 420) (e.g., the processing circuit(s) of the processor 210) may extract image information of the image. The image information of the image may include element values of elements in the image. An element may be a pixel if the image is two-dimensional (2D) or a voxel if the image is three-dimensional (3D).

In 530, the processing device 120 (e.g., the second obtaining module 430) (e.g., the processing circuit(s) of the processor 210) may obtain feature information of the region of interest (ROI) in the object.

The term "region of interest (ROI)" used in this present disclosure refers to a physical portion of an object (e.g., a tissue, an organ, a lesion, a portion including an organ or tissue), or a region in an image of the object that includes a representation of the physical portion.

In some embodiments, the processing device 120 may obtain an initial image (e.g., a locator image) of the object by performing a preliminary scan (e.g., the locator scan) on the object. For example, the processing device 120 may direct the imaging device 110 to perform the locator scan on the object to obtain the initial image. The processing device 120 may obtain marking information of the ROI from the initial image of the object. The marking information of the ROI may be marked by a user (e.g., a doctor) on the initial image of the object and stored in the storage device (e.g., the storage device 150, the storage 220, and/or the storage 390). In some embodiments, the marking information of the ROI may be obtained based on an automated image segmentation in which the ROI is segmented from the initial image. The processing device 120 may obtain the marking information of the ROI from the initial image of the object or the storage device via a network (e.g., the network 140).

The marking information may include a size of the ROI, a shape of the ROI, a position of the ROI in the initial image, or the like, or any combination thereof. The size of the ROI may include a length, a width, a diameter, a major axis, a minor axis, an area of the ROI, or the like, or any combination thereof. The shape of the ROI may include a polygon (e.g., a quadrilateral, a pentagon, a hexagon, a rectangle, etc.), a circle, a sector, an ellipse, or the like, or any combination thereof. Different shapes of ROI may be described by different sizes. For example, when the shape of the ROI is a circle, the size of the ROI may include a diameter, a radius, or an area of the ROI. The size and shape used to describe an ROI may be determined based on a default value of the medical system 100, manually set by a user or an operator, or determined by the processing device 120 according to an actual need. In some embodiments, the size and shape of the ROI may also be referred to as geometric information of the ROIL The position of the ROI in the initial image may include coordinates of pixels in the ROI in the initial image, coordinates of boundary of the ROI in the initial image, coordinates of specific points (e.g., a center point, a corner point, etc.) in the ROI in the initial image, or the like, or any combination thereof. It should be noted that the marking information described above is merely provided for illustration purposes, and not intended to limit the scope of the present disclosure.

According to the marking information of the ROI, the processing device 120 may obtain the feature information of the ROI. The feature information of the ROI may include the size of the ROI, the shape of the ROI, an anatomical feature of the ROI in the image, imaging parameter information associated with the ROI in the image, pixel information associated with the ROI in the image, or the like, or any combination thereof. The anatomical feature of the ROI may include a morphology, a structure, a composition, an anatomical name, etc., of an organ or tissue in the ROI. The imaging parameter information associated with the ROI may include CT values of the pixels in the ROI in the image, an average CT value of the ROI in the image, a variance of the CT values of the ROI in the image, a contrast of the ROI in a subtraction image of the image, or the like, or any combination thereof. The CT values of the ROI may indicate the attenuation distribution of the radiation beams that traverse the ROI. In some embodiments, the CT values may be represented in Hounsfield units (HU), a dimensionless unit expressing the CT values in a standardized and convenient form. Merely by way of example, the CT value of distilled water at standard temperature and pressure (STP) may be 0 HU, and the CT value of air at STP may be −1000 HU, The subtraction image of the image may be obtained based on the image and the initial image. For example, the image and the initial image may both be MR images, and the processing device 120 may obtain the subtraction image of the image by subtracting the initial image from the image; the ROI may be indicated by a different contrast relative to the surroundings of the ROI in the subtraction image of the image. The pixel information associated with the ROI may include pixel values of pixels in the ROI, an average pixel value of pixels in the ROI, a variance of the pixel values of pixels in the ROI, voxel values of voxels in the ROI, an average voxel value of voxels in the ROI, a variance of the voxel values of voxels in the ROI, or the like, or any combination thereof.

In some embodiments, the processing device 120 may directly extract information from the marking information of the ROI as the feature information of the ROI. For example, the processing device 120 may directly extract the size and/or the shape of the ROI from the marking information of the ROI as the feature information of the ROI. In some embodiments, the processing device 120 may obtain the feature information of the ROI based on the position of the ROI in the marking information of the ROI. For example, the processing device 120 may obtain the imaging parameter information and/or the pixel information associated with the ROI from the image based on the position of the ROI in the initial image.

In 540, the processing device 120 (e.g., the determination module 440) (e.g., the processing circuit(s) of the processor 210) may determine position information of the ROI in the image using a positioning model based on the image information of the image and the feature information of the ROI.

The position information of the ROI in the image may include coordinates of pixels in the ROI in the image, coordinates of the boundary of the ROI in the image, coordinates of specific points (e.g., a center point, a corner point, etc.) in the ROI in the image, or the like, or any combination thereof.

In some embodiments, the positioning model may be pre-trained and stored in a storage device (e.g., the storage device 150, the storage 220, and/or the storage 390) disclosed elsewhere in the present disclosure. The processing device 120 may retrieve the positioning model from the storage device. In some embodiments, the positioning model may include a machine learning model, a regression model, or the like, or any combination thereof. The machine learning model may include a decision tree model, a neural network model, a naive Bayesian model (NEM), a k-nearest neighbor (KNN) model, a support vector machine (SVM), or the like, or any combination thereof. The regression model may include a linear regression model, a logistic regression model, a polynomial regression model, a stepwise regression model, a ridge regression model, a lasso regression model, an elastic net regression model, or the like, or any combination thereof. In some embodiments, the positioning model may be trained based on a plurality of training samples. More descriptions regarding the positioning model may be found elsewhere in the present disclosure (e.g., FIG. 7 and the description thereof).

In some embodiments, the processing device 120 may input the image information of the image and the feature information of the ROI into the positioning model. Further, the processing device 120 may determine the position information of the ROI in the image based on an output of the positioning model. In the present disclosure, the use of the positioning model may allow for a dynamic determination of the position information of the ROI over the course of a medical procedure (e.g., an imaging procedure, a treatment procedure) and improve the accuracy of the obtained position information of the ROI, thereby improving the accuracy of ROI monitoring (e.g., concentration monitoring of a contrast agent) based on the position information of the ROI.

In some embodiments, the processing device 120 may preprocess the image information of the image and/or the feature information of the ROI and determine the position information of the ROI in the image based on the preprocessed image information and/or the preprocessed feature information of the ROI. For example, the processing device 120 may input the preprocessed image information and the preprocessed feature information into the positioning model and determine the position information of the ROI in the image based on an output of the positioning model, Merely by way of example, the preprocessing may include data cleaning, normalization, data transformation, or the like, or any combination thereof. The data cleaning may refer to a process of checking and verifying data/information to remove duplicate data/information and correct existing errors in the data/information. The data transformation may refer to a process of changing data/information from one representation to another.

In some embodiments, the processing device 120 may update the feature information of the ROI based on the position information of the ROI in the image. Further, the processing device 120 may determine whether updated imaging parameter information associated with the ROI satisfies a condition relating to a concentration of a contrast agent. According to a determination result of whether the updated imaging parameter information associated with the ROI satisfies the condition, the processing device 120 may perform imaging operations. For example, when the updated imaging parameter information associated with the ROI satisfies the condition, the imaging operations may include obtaining a second image of the object captured by the imaging device (e.g., the imaging device 110) at a second time point subsequent to a first time point when the image is acquired; identifying the ROI in the second image using the positioning model based on image information of the second image and feature information of the ROI in the second image, and determining whether updated imaging parameter information associated with the ROI in the second image satisfies the condition. When the updated imaging parameter information associated with the ROI does not satisfy the condition, the imaging operations may include performing a medical procedure (e.g., an imaging procedure, a treatment procedure) on the object. More descriptions regarding the imaging operations may be found elsewhere in the present disclosure (e.g., FIG. 6 and the description thereof).

It should be noted that the above description regarding the process 500 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 500 may be accomplished with one or more additional operations not described and/or without one or more of the operations discussed above. For example, the process 500 may include an additional transmitting operation in which the processing device 120 may transmit the position information of the ROI to the terminal device 130. As another example, the process 500 may include an additional storing operation in which the processing device 120 may store information and/or data (e.g., the image of the object, the image information of the image, the feature information of the ROI, the position information of the ROI) associated with the ROI positioning in a storage device (e.g., the storage device 150, the storage 220, the storage 390) disclosed elsewhere in the present disclosure.

Figure 6:
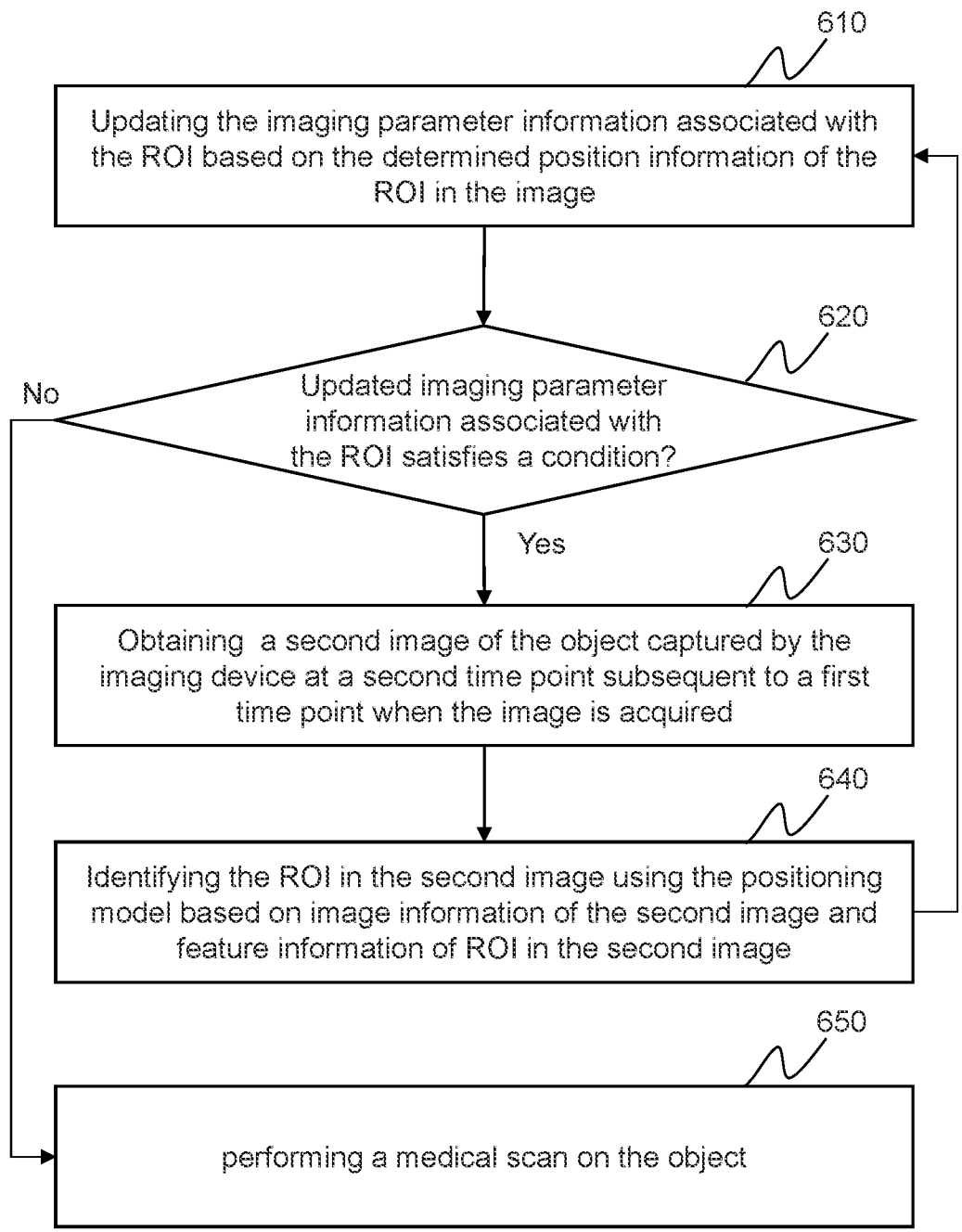
FIG. 6 is a flowchart illustrating exemplary imaging operations associated with the ROI positioning according to some embodiments of the present disclosure.

FIG. 6 is a flowchart illustrating exemplary imaging operations associated with the ROI positioning according to some embodiments of the present disclosure. In some embodiments, process 600 may be executed by the medical system 100. For example, the process 600 may be implemented as a set of instructions (e.g., an application) stored in a storage device (e.g., the storage device 150, the storage 220, and/or the storage 390). In some embodiments, the processing device 120 (e.g., the processor 210 of the computing device 200, the CPU 340 of the mobile device 300, and/or one or more modules illustrated in FIG. 4) and/or the ROI processing device 1000 (e.g., one or more modules illustrated in FIG. 10) may execute the set of instructions and may accordingly be directed to perform the process 600. The operations of the illustrated process presented below are intended to be illustrative. In some embodiments, the process 600 may be accomplished with one or more additional operations not described and/or without one or more of the operations discussed. Additionally, the order of the operations of process 600 illustrated in FIG. 6 and described below is not intended to be limiting.

In 610, the processing device 120 (e.g., the determination module 440) (e.g., the processing circuit(s) of the processor 210) may update imaging parameter information associated with an ROI based on position information of the ROI in an image. As used herein, the image may refer to an image that is obtained in operation 510 in FIG. 5 and the position information may refer to position information that is determined in operation 540 in FIG. 5.

As described in connection with FIG. 5, the imaging parameter information associated with the ROI may include CT values of the ROI, an average CT value of the ROI, a variance of the CT values of the ROI, a contrast of the ROI in a subtraction image of the image, or the like, or any combination thereof.

In some embodiments, due to factors such as a rigid motion of the object, respiratory motion of the object, etc., a position of the ROI in the image (e.g., a tracker image) may change relative to a position of the ROI in an initial image (e.g., a locator image) or a previous image that is obtained at a time point before the image is acquired. In addition, due to a concentration of a contrast agent changes over time, the imaging parameter information (e.g., the CT values of the ROI, the average CT value of the ROI, the variance of the CT values of the ROI, the contrast of the ROI in the subtraction image of the image) associated with the ROI in the image may change relative to imaging parameter information associated with the ROI in the initial image or the previous image. Therefore, the processing device 120 may update the imaging parameter information (e.g., the CT values of the ROI, the average CT value of the ROI, the variance of the CT values of the ROI, the contrast of the ROI in the subtraction image of the image) associated with the ROI based on the position information (e.g., coordinates of pixels in the ROI) of the ROI in the image. For example, the processing device 120 may obtain updated CT values of the ROI from the image based on the coordinates of pixels in the ROI in the image, and then determine updated average CT value of the ROI and updated variance of the CT values of the ROI. As another example, when the image is an MR image, the processing device 120 may obtain updated contrast of the ROI from a subtraction image of the MR image based on the coordinates of pixels in the ROI in the image.

In 620, the processing device 120 (e.g., the determination module 440) (e.g., the processing circuit(s) of the processor 210) may determine whether the updated imaging parameter information (e.g., the updated CT values of the ROI, the updated average CT value of the ROI, the updated variance of the CT values of the ROI, the updated contrast of the ROI in the subtraction image of the image) associated with the ROI satisfies a condition relating to a concentration of a contrast agent.

In some embodiments, the imaging parameter information associated with the ROI may be associated with a concentration of the contrast agent in the ROI. For example, the higher the CT values, or the average CT value of the ROI, the contrast of the ROI in the subtraction image of the image, the higher the concentration of contrast agent.

Further, the processing device 120 may perform imaging operations based on a determination result of whether the imaging parameter information associated with the ROI satisfies a condition. For example, the condition may include a threshold; the processing device 120 may determine whether the updated imaging parameter information (e.g., the CT values, the average CT value, the variance of the CT values, the contrast of the ROI in the subtraction image of the image) associated with the ROI exceeds the threshold. The threshold may be a default value of the medical system 100, manually set by a user or an operator, or determined by the processing device 120 according to an actual need. Merely by way of example, the threshold may be a CT value or a contrast value that indicates a concentration of a contrast agent required for clinical use. In some embodiments, the determination result may include that the updated imaging parameter information associated with the ROI satisfies the condition relating to the threshold. When the updated imaging parameter information associated with the ROI is less than a threshold, that is, the concentration of the contrast agent in the ROI does not meet the clinical need, the processing device 120 may determine that the updated imaging parameter information associated with the ROI satisfies the condition. In response to determining that the updated imaging parameter information associated with the ROI satisfies the condition, the processing device 120 may perform operations 630-640. In some embodiments, the determination result may include that the updated imaging parameter information associated with the ROI does not satisfy the condition relating to the threshold. For example, when the updated imaging parameter information (e.g., the updated CT values, the updated average CT value, the updated variance of the CT values, the updated contrast of the ROI in the subtraction image of the image) associated with the ROI exceeds the threshold, that is, the concentration of the contrast agent in the ROI meets the clinical need, the processing device 120 may determine that the updated imaging parameter information associated with the ROI does not satisfy the condition. In response to determining that the updated imaging parameter information associated with the ROI does not satisfy the condition, the processing device 120 may perform operation 650.

In 630, the processing device 120 (e.g., the first obtaining module 410) (e.g., the interface circuit(s) of the processor 210) may obtain a second image of the object using imaging data acquired by the imaging device (e.g., the imaging device 110) at a second time point subsequent to a first time point when imaging data corresponding to the image is acquired. The obtaining of the second image of the object may be performed in a similar manner as that of operation 510 described in connection with FIG. 5, and the descriptions thereof are not repeated here.

In 640, the processing device 120 (e.g., the determination module 440) (e.g., the processing circuit(s) of the processor 210) may identify the ROI in the second image using the positioning model based on image information of the second image and feature information of the ROI in the second image. The image information of the second image may include pixel values of pixels in the second image. The feature information of the ROI in the second image may include the size of the ROI, the shape of the ROI, an anatomical feature of the ROI in the second image, imaging parameter information associated with the ROI in the second image, or pixel information associated with the ROI in the second image, or the like, or any combination thereof. The identification of the ROI in the second image may be performed in a similar manner as that of operation 540 described in connection with FIG. 5, and the descriptions thereof are not repeated here.

Further, the processing device 120 may designate the second image as the image and repeat operations 610-620. In some embodiments, the process 600 may be terminated manually by a user or an operator or by the processing device 120 according to a termination condition. An exemplary termination condition may include that at least a portion of the process 600 (e.g., 610 and 620) has been performed a certain number of times.

In some embodiments, the processing device 120 may determine a curve indicating a change of the updated imaging parameter information associated with the ROI corresponding to a plurality of images (e.g., the image, the second image) whose imaging data are acquired at different time points. A point on the curve may correspond to one image and indicate a value (e.g., an average CT value) of the imaging parameter information associated with the ROI in the image. Further, the processing device 120 may transmit the curve to a terminal device for displaying. Merely by way of example, the curve may also be displayed by other components (e.g., the imaging device 110, the processing device 120) of the medical system 100.

In 650, the processing device 120 (e.g., the determination module 440) (e.g., the processing circuit(s) of the processor 210) may perform a medical procedure on the object.

In some embodiments, the medical procedure may include an imaging procedure to acquire imaging data relating to the object. Exemplary imaging procedure may include a CT scan, a PET scan, an X-ray scan, an MR scan, a single-photon emission computed tomography (SPECT) scan, an ultrasonography scan, a digital radiography (DR) scan, or the like, or any combination thereof. In some embodiments, the medical procedure may include a treatment procedure to deliver a radiotherapy treatment to the object. Exemplary treatment procedure may include a conformal radiation therapy session, an image-guided radiation therapy (IGRT) session, an intensity-modulated radiation therapy (IMRT) session, an intensity-modulated arc therapy (IMAT) session, an emission guided radiation therapy (EGRT) session, or the like, or any combination thereof.

It should be noted that the above description regarding the process 600 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 7:
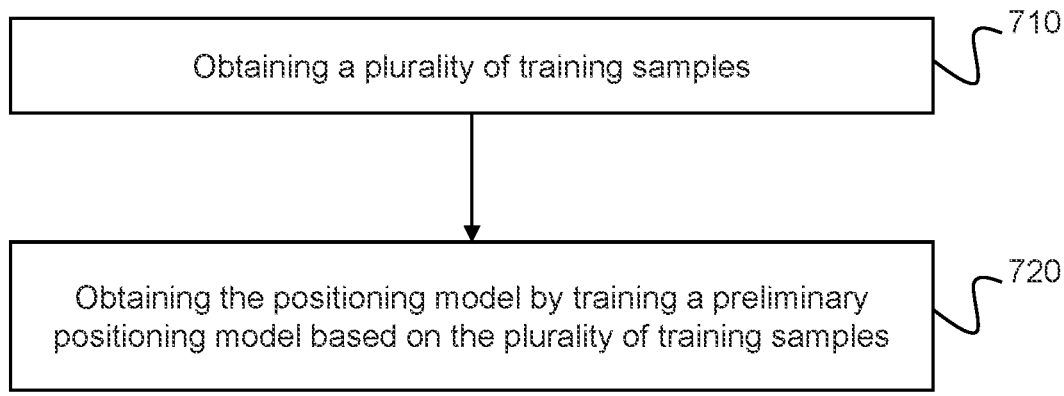
FIG. 7 is a flowchart illustrating an exemplary process for determining a positioning model according to some embodiments of the present disclosure.

FIG. 7 is a flowchart illustrating an exemplary process for determining a positioning model according to some embodiment of the present disclosure In some embodiments, process 700 may be executed by the medical system 100. For example, the process 700 may be implemented as a set of instructions (e.g., an application) stored in a storage device (e.g., the storage device 150, the storage 220, and/or the storage 390). In some embodiments, the processing device 120 (e.g., the processor 210 of the computing device 200, the CPU 340 of the mobile device 300, and/or one or more modules illustrated in FIG. 4) and/or the ROI processing device 1000 (e.g., one or more modules illustrated in FIG. 10) may execute the set of instructions and may accordingly be directed to perform the process 700. Alternatively, the process 700 may be performed by a computing device of a system of a vendor that provides and/or maintains such a positioning model. The operations of the illustrated process presented below are intended to be illustrative. In some embodiments, the process 700 may be accomplished with one or more additional operations not described and/or without one or more of the operations discussed. Additionally, the order of the operations of process 700 illustrated in FIG. 7 and described below is not intended to be limiting.

In 710, the processing device 120 (e.g., the training module 450) (e.g., the processing circuit(s) of the processor 210) may obtain a plurality of training samples from various sample objects. In some embodiments, the sample objects may be of a same type. For instance, the sample objects may include a same type of organ or tissue from different patients. A type of the sample objects may be related to a function of a positioning model. For example, a positioning model suitable for a specific organ and tissue may be trained by a plurality of training samples that are obtained from the specific organ and tissue.

In some embodiments, each of the plurality of training samples may include a sample image, image information of the sample image, an ROI in the sample image, feature information of the ROI in the sample image, and reference position information of the ROI in the sample image, or the like, or any combination thereof. The sample image may refer to an image obtained based on a sample object. For example, the sample image may be an image of a sample object acquired by the imaging device 110 or other external imaging devices. A sample object may be of a same type as the object. The image information of the sample image may include pixel values of pixels or voxel values of voxels in the sample image. Similar to what is described in connection with FIG. 6, the ROI (e.g., the marking information of the ROI) in the sample image may be obtained by marking an initial image (e.g., a locator image) of the sample object by a user (e.g., a doctor). The feature information of the ROI in the sample image may include a size of the ROI, a shape of the ROI, an anatomical feature of the ROI in the sample image, imaging parameter information associated with the ROI in the sample image, pixel information associated with the ROI in the sample image, or the like, or any combination thereof. The reference position information of the ROI may refer to qualified position information (e.g., position information of clinically acceptable or high accuracy) of the ROI in the sample image. In some embodiments, the reference position information of the ROI may be determined manually by the user (e.g., the doctor) on the sample image. In some embodiments, the reference position information of the ROI may be determined based on an automated image segmentation in which the ROI is segmented from the sample image.

In some embodiments, at least one of the plurality of training samples may be previously generated and stored in a storage device (e.g., the storage device 150, the storage 220, the storage 390, or an external storage device) disclosed elsewhere in the present disclosure. The processing device 120 may retrieve the plurality of training samples directly from the storage device. In some embodiments, at least a portion of the plurality of training samples may be generated by the processing device 120. Merely by way of example, the processing device 120 may direct the imaging device 110 to perform a scan on a sample object (e.g., a patient) to obtain a sample image.

In 720, the processing device 120 (e.g., the training module 450) (e.g., the processing circuit(s) of the processor 210) may obtain the positioning model by training a preliminary positioning model based on the plurality of training samples.

In some embodiments, the preliminary positioning model may include a machine learning model, a regression model, or the like, or any combination thereof. As described in connection with FIG. 5, the machine learning model may include a decision tree model, a neural network model (e.g., a convolutional neural network (CNN) model), a naive Bayesian model (NBM), a k-nearest neighbor (KNN) model, a support vector machine (SVM), or the like, or any combination thereof. The regression model may include a linear regression model, a logistic regression model, a polynomial regression model, a stepwise regression model, a ridge regression model, a lasso regression model, an elastic net regression model, or the like, or any combination thereof. In some embodiments, the preliminary positioning model may include at least one preliminary model parameter. The at least one preliminary model parameter may be set according to a default setting of the medical system 100 or may be adjustable under different situations. Taking a convolutional neural network (CNN) model as an example, the at least one preliminary model parameter may include a count of convolutional layers, a count of kernels, a kernel size, a stride, a padding of each convolutional layer, or the like, or any combination thereof.

In some embodiments, the processing device 120 may train the preliminary positioning model iteratively until a termination condition is satisfied. In response to that the termination condition is satisfied, the positioning model may be finalized. In some embodiments, the termination condition may relate to a value of a loss function. For example, the termination condition may be deemed satisfied if the value of the loss function is minimal or smaller than a predetermined threshold. As another example, the termination condition may be deemed satisfied if the value of the loss function converges. In some embodiments, "convergence" may refer to that the variation of the values of the loss function in two or more consecutive iterations is equal to or smaller than a predetermined threshold. In some embodiments, "convergence" may refer to that a difference between the value of the loss function and a target value is equal to or smaller than a predetermined threshold. In some embodiments, the termination condition may be deemed satisfied when a specified count of iterations have been performed in the training process.

In each iteration, the image information of the sample image and the feature information of the ROI in the sample image may be used as an input of the preliminary positioning model or an intermediate positioning model obtained in a previous iteration. The preliminary or intermediate positioning model may generate estimated position information of the ROI in the sample image. Values of model parameters of the preliminary positioning model may be updated by comparing the reference position information of the ROI in the sample image and the estimated position information of the ROI in the sample image.

In some embodiments; the generation and/or updating of the positioning model may be performed on a processing device (e.g., the processing device 120), while the application of the positioning model may be performed on a different processing device (e.g., a processing device independent from the processing device 120). In some embodiments, the generation and/or updating of the positioning model may be performed on a processing device of a system different from the medical system 100 or a server different from a server including the processing device 120 on which the application of the positioning model is performed. For instance, the generation and/or updating of the positioning model may be performed on a first system of a vendor who provides and/or maintains such a positioning model and/or has access to training samples used to generate the positioning model, while ROI positioning based on the provided positioning model may be performed on a second system of a client of the vendor. In some embodiments, the generation and/or updating of the positioning model may be performed online in response to a request for ROI positioning. In some embodiments, the generation and/or updating of the positioning model may be performed offline.

In some embodiments, the positioning model may be generated and/or updated (or maintained) by, e.g., the manufacturer of the imaging device 110 or a vendor. For instance, the manufacturer or the vendor may load the positioning model into the medical system 100 or a portion thereof (e.g., the processing device 120) before or during the installation of the imaging device 110 and/or the processing device 120, and maintain or update the positioning model from time to time (periodically or not). For example, the manufacturer or the vendor may update the positioning model periodically or irregularly based on one or more newly-generated training samples (e.g., new sample images). The maintenance or update may be achieved by installing a program stored on a storage device (e.g., a compact disc, a USB drive, etc.) or retrieved from an external source (e.g., a server maintained by the manufacturer or vendor) via the network 140. The program may include a new model (e.g., a new positioning model) or a portion of a model that substitutes or supplements a corresponding portion of the model.

It should be noted that the above description regarding the process 700 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be added or omitted. As another example, the processing device 120 may divide the plurality of training samples into a training set and a test set. The training set may be used to train the model and the test set may be used to determine whether the training process has been completed.

Figure 8:
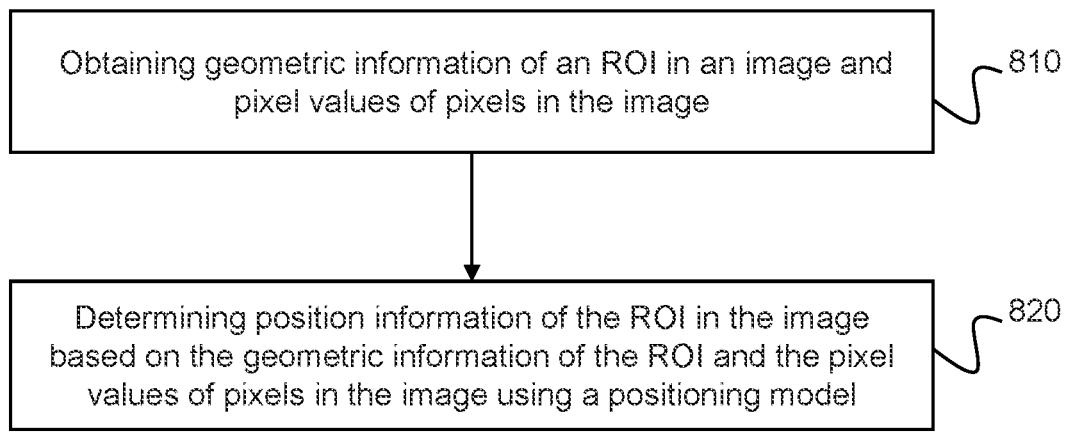
FIG. 8 is a flowchart illustrating an exemplary process for processing an ROI according to some embodiments of the present disclosure.

FIG. 8 is a flowchart illustrating an exemplary process for processing an ROI according to some embodiments of the present disclosure. In some embodiments, process 800 may be executed by the medical system 100. For example, the process 800 may be implemented as a set of instructions (e.g., an application) stored in a storage device (e.g., the storage device 150, the storage 220, and/or the storage 390). In some embodiments, the processing device 120 (e.g., the processor 210 of the computing device 200, the CPU 340 of the mobile device 300, and/or one or more modules illustrated in FIG. 4) and/or the ROI processing device 1000 (e.g., one or more modules illustrated in FIG. 10) may execute the set of instructions and may accordingly be directed to perform the process 800. The operations of the illustrated process presented below are intended to be illustrative. In some embodiments, the process 800 may be accomplished with one or more additional operations not described and/or without one or more of the operations discussed. Additionally, the order of the operations of process 800 illustrated in FIG. 8 and described below is not intended to be limiting.

The process 800 may be applied in a dynamic tracking of an ROI in an image sequence (e.g., one or more images that are sequentially obtained) of a same object during a medical imaging. The medical imaging may include a CT scan, a PET scan, an X-ray scan, an MR scan, or the like, or any combination thereof. For illustration purposes, the process 800 is described with reference to the dynamic ROI tracking in a process of contrast agent tracking scan (also referred to as bolus tracking).

In 810, geometric information of an ROI in an image and pixel values of pixels in the image may be obtained. In some embodiments, operation 810 may be performed by the processing device 120 (e.g., the second obtaining module 430 illustrated in FIG. 4) (e.g., the processing circuit(s) of the processor 210) and/or the ROI processing device 1000 (e.g., an information obtaining module 1010 illustrated in FIG. 10).

As described in connection with FIG. 5, a contrast agent tracking scan (also referred to as bolus tracking) may include a locator scan that is used to determine an initial region of interest (ROI) in the object and one or more tracker scans that are sequentially performed to monitor a concentration of a contrast agent in the ROI. The image (also referred to as a concentration tracking image) may be obtained by performing each of the one or more tracker scans on an object. Traditionally, the one or more tracker scans are performed under a premise that the position of the ROI remains unchanged (i.e., the ROI is static). However, in fact, due to factors such as a rigid motion of the object, respiratory motion of the object, etc., the position of the ROI may change after the locator scan, which may decrease the accuracy of the concentration monitoring of the contrast agent, thereby affecting the image quality of an image obtained in the subsequent medical procedure. To address the above-mentioned problems, in this embodiment, a position of the ROI during each tracker scan may be redetermined (i.e., dynamically tracked). Specifically, during each tracker scan, the position information of the ROI may be re-evaluated based on relevant information (e.g., geometric information of the ROI) of an initial ROI marked during the locator scan and the pixel values of pixels in an image obtained during the tracker scan.

In some embodiments, before the one or more tracker scans are performed, a locator scan may be performed to determine an initial image (e.g., a locator image) of the object. In some embodiments, a user (e.g., a doctor) may mark an initial ROI in the initial image. In some embodiments, the initial ROI in the initial image may be marked based on an automated image segmentation in which the initial ROI is segmented from the initial image. Further, the geometric information of the ROI may be obtained by extracting geometric information of the initial ROI from the initial image. The geometric information of the ROI may include a shape and size of the ROI. During the one or more tracker scans are performed, although the position of the ROI may vary, the shape and size of the ROI remain unchanged. Therefore, the geometric information of the initial ROI in the initial image may be regarded as the geometric information of the ROI in the image. Exemplary size of the ROI may include a diameter, a length, a width, a major axis, a minor axis of the ROI, or the like, or any combination thereof. Exemplary shape of the ROI may include a rectangle, a circle, an ellipse, or the like, or any combination thereof.

In some embodiments, the size of the ROI may be set based on the shape of the ROI. For example, when the ROI is a rectangle, the size of the ROI may include the length and width of the ROI; when the ROI is a circle, the size of the ROI may include the diameter of the ROI; when the ROI is an ellipse, the size of the ROI may include the major axis and the minor axis of the ROI. The advantage of the above setting is that the geometric information of the ROI may be obtained more conveniently and accurately and the accuracy of the subsequent ROI positioning may be improved.

In 820, position information of the ROI in the image may be determined based on the geometric information of the ROI and the pixel values of pixels in the image using a positioning model. In some embodiments, operation 820 may be performed by the processing device 120 (e.g., the determination module 440 illustrated in FIG. 4) (e.g., the processing circuit(s) of the processor 210) and/or the ROI processing device 1000 (e.g., a position information determination module 1020 illustrated in FIG. 10).

In some embodiments, the positioning model may be trained based on a plurality of training samples. Specifically, the plurality of training samples may be obtained. Each of the plurality of training samples may include a sample image, pixel values of pixels in the sample image, geometric information of an ROI in the sample image, and reference position information of the ROI in the sample image. Merely by way of example, ROI positioning images obtained in previous contrast agent tracking scans may be used as sample images. The pixel values of pixels and the ROI in each sample image may be extracted from the sample image. Further, geometric information of the ROI and reference position information of the ROI may be obtained from the sample image. The positioning model may be obtained by training a preliminary positioning model based on the plurality of training samples. The preliminary positioning model may include a machine learning model, a regression model, or the like, or any combination thereof. The positioning model in this embodiment may be used to establish a relationship between the geometric information of an ROI in an image and pixel values of pixels in the image and position information of the ROI in the image. Therefore, the machine learning model or the regression model that is capable of establishing the relationship may be selected as the preliminary positioning model. In this embodiment, the positioning model may be used to dynamically position an ROI in an image, which may improve the convenience and efficiency of determining the position information of the ROI in the image. More descriptions regarding the positioning model may be found elsewhere in the present disclosure (e.g., FIG. 7 and the description thereof).

In some embodiments, the geometric information of the ROI and the pixel values of pixels in the image may be input into the positioning model, and an output of the positioning model may be the position information of the ROI in the image.

In some embodiment, the geometric information of an ROI in an image and the pixel values of pixels in the image may be obtained, and then the position information of the ROI in the image may be determined based on the geometric information of the ROI and the pixel values of pixels in the image using a positioning model, which realizes the dynamic determination of the position of the ROI in each image during the process of acquiring the image sequence and solves the problem of the inaccurate position of static ROI, thereby improving the positioning accuracy of the ROI and the accuracy of the concentration monitoring of the contrast agent.

It should be noted that the above description regarding the process 800 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 9:
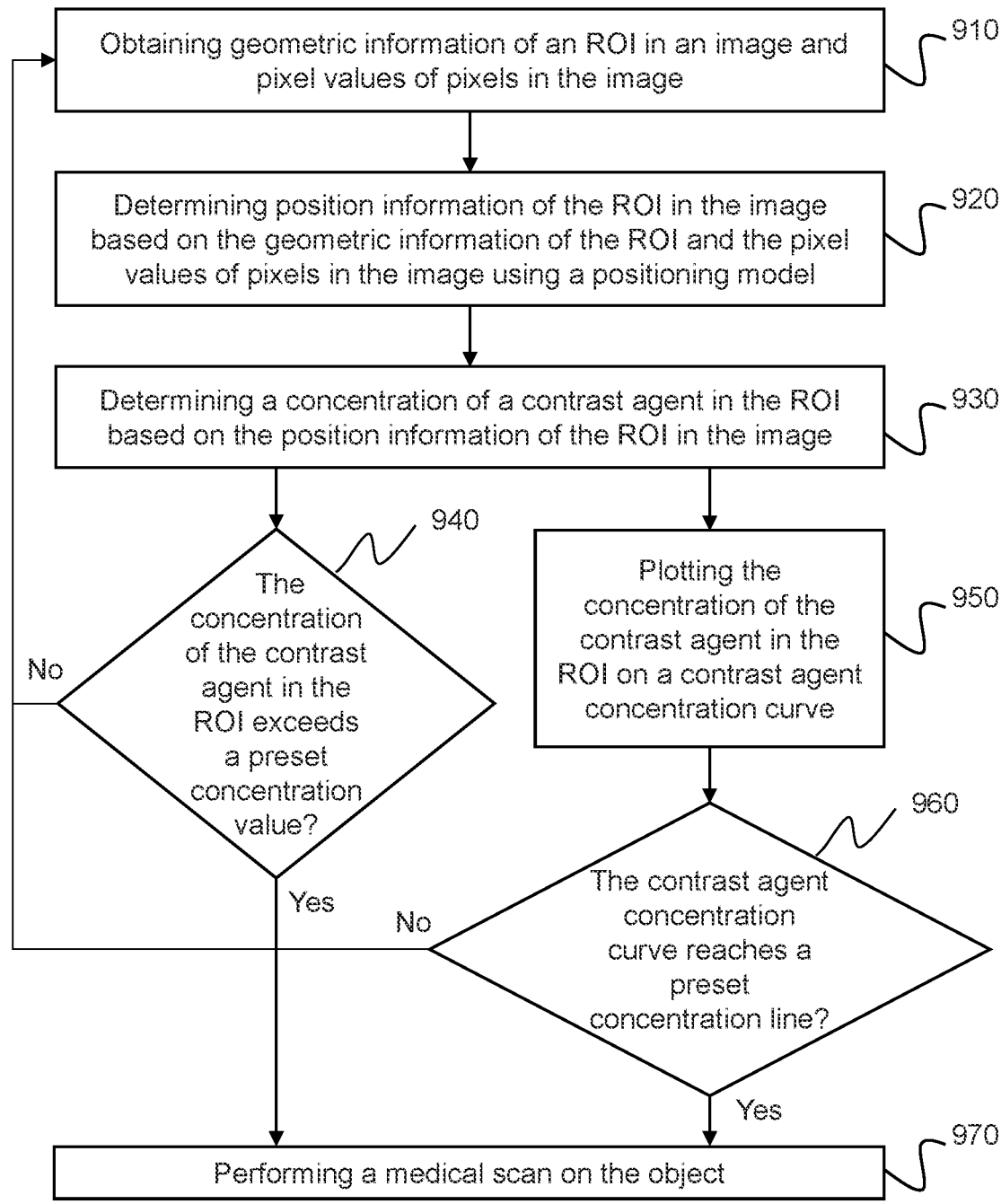
FIG. 9 is a flowchart illustrating an exemplary process for processing an ROI according to some embodiments of the present disclosure.

FIG. 9 is a flowchart illustrating an exemplary process for processing an ROI according to some embodiments of the present disclosure. In some embodiments, process 900 may be executed by the medical system 100. For example, the process 900 may be implemented as a set of instructions (e.g., an application) stored in a storage device (e.g., the storage device 150, the storage 220, and/or the storage 390). In some embodiments, the processing device 120 (e.g., the processor 210 of the computing device 200, the CPU 340 of the mobile device 300, and/or one or more modules illustrated in FIG. 4) and/or the ROI processing device 1000 (e.g., one or more modules illustrated in FIG. 10) may execute the set of instructions and may accordingly be directed to perform the process 900. The operations of the illustrated process presented below are intended to be illustrative. In some embodiments, the process 900 may be accomplished with one or more additional operations not described and/or without one or more of the operations discussed. Additionally, the order of the operations of process 900 illustrated in FIG. 9 and described below is not intended to be limiting.

In 910, geometric information of an ROI in an image and pixel values of pixels in the image may be obtained. As described in connection with FIG. 5, the image may be obtained by performing each of the one or more tracker scans on an object. Operation 910 may be performed in a similar manner as operation 810 as described in connection with FIG. 8, and the descriptions thereof are not repeated here.

In 920, position information of the ROI in the image may be determined based on the geometric information of the ROI and the pixel values of pixels in the image using a positioning model. Operation 920 may be performed in a similar manner as operation 820 as described in connection with FIG. 8, and the descriptions thereof are not repeated here.

In 930, a concentration of a contrast agent in the ROI may be determined based on the position information of the ROI in the image. In some embodiments, operation 930 may be performed by the processing device 120 (e.g., the determination module 440 illustrated in FIG. 4) (e.g., the processing circuit(s) of the processor 210) and/or the ROI processing device 1000 (e.g., a contrast agent concentration determination module 1030 illustrated in FIG. 10).

In some embodiments, CT values of the ROI may be obtained based on the position information of the ROI in the image. Further, the concentration of the contrast agent in the ROI may be determined based on the CT values of the ROI. Merely by way of example, the CT values of the ROI may be proportional to the concentration of the contrast agent in the ROI. In some embodiments, pixel values of pixels in the ROI may be extracted from the image based on the position information of the ROI in the image. Further, the concentration of the contrast agent in the ROI may be determined based on pixel values of pixels in the ROI.

In 940, whether the concentration of the contrast agent in the ROI exceeds a preset concentration value may be determined. In some embodiments, operation 940 may be performed by the processing device 120 (e.g., the determination module 440 illustrated in FIG. 4) (e.g., the processing circuit(s) of the processor 210) and/or the ROI processing device 1000 (e.g., the first circulation control module 1040 illustrated in FIG. 10).

In some embodiments, when the concentration of the contrast agent in the ROI exceeds the preset concentration value, that is, the concentration of the contrast agent meets a clinical need, operation 970 may be performed. The preset concentration value may be a default value of the medical system 100, manually set by a user or an operator, or determined by the processing device 120 according to a clinical need.

In some embodiments, when the concentration of the contrast agent in the ROI is less than the preset concentration value, that is, the concentration of the contrast agent does not meet the clinical need, a second image may be obtained and operations 910-930 may be performed based on the second image.

In 950, the concentration of the contrast agent in the ROI may be plotted on a contrast agent concentration curve. In some embodiments, operation 950 may be performed by the processing device 120 (e.g., the determination module 440 illustrated in FIG. 4) (e.g., the processing circuit(s) of the processor 210) and/or the ROI processing device 1000 (e.g., a second circulation control module 1050 illustrated in FIG. 10).

The contrast agent concentration curve may refer to a curve composed of concentrations of the contrast agent in the ROI corresponding to a plurality of images acquired at different time points. The contrast agent concentration curve may indicate a change (e.g., a change process, a change trend) of the concentrations of the contrast agent in the ROI. After the contrast agent concentration curve is determined, the contrast agent concentration curve may be transmitted to a terminal device (e.g., the terminal device 130) for displaying. A user may view the contrast agent concentration curve on an interface of the terminal device.

In 960, whether the contrast agent concentration curve reaches a preset concentration line or the preset concentration value may be determined. In some embodiments, operation 960 may be performed by the processing device 120 (e.g., the determination module 440 illustrated in FIG. 4) (e.g., the processing circuit(s) of the processor 210) and/or the ROI processing device 1000 (e.g., the second circulation control module 1050 illustrated in FIG. 10).

In some embodiments, when the contrast agent concentration curve reaches the preset concentration line or the preset concentration value, that is, the concentration of the contrast agent meets a clinical need, operation 970 may be performed. The preset concentration line may be a default value of the medical system 100, manually set by a user or an operator, or determined by the processing device 120 according to a clinical need.

In some embodiments, when the contrast agent concentration curve does not reach the preset concentration line or the preset concentration value, that is, the concentration of the contrast agent does not meet the clinical need, a second image may be obtained and operations 910-930 and 950 may be performed based on the second image.

In some embodiments, the preset concentration line may be displayed on the interface of the terminal device, which may enable the user to more intuitively check whether the contrast agent concentration curve reaches the preset concentration line.

In some embodiments, operation 940 and operations 950-960 may be executed alternatively. For example, operation 940 may be executed while operations 950-960 are not executed. As another example, operations 950-960 may be executed while operation 940 is not executed. In some embodiments, operation 940 and operations 950-960 may be executed in tandem. When operation 940 and operations 950-960 are executed in tandem, operation 940 and operations 950-960 may be executed in one of various orders. For example, operation 940 may be executed first, and then operations 950-960 may be executed. As another example, operations 950-960 may be executed first, and then operation 940 may be executed. As a further example, operation 940 and operations 950-960 may be executed simultaneously.

In 970, a medical procedure may be performed on the object. An image obtained by the medical procedure may be used for lesion identification or treatment. Operation 970 may be performed in a similar manner as operation 650 as described in connection with FIG. 6, and the descriptions thereof are not repeated here.

In this embodiment, after the position information of the ROI in the image is determined, a concentration of a contrast agent in the ROI may be determined based on the position information of the ROI in the image, which realizes the monitoring of the concentration of the contrast agent in the ROI in the image. The precise positioning of the ROI in the image may improve the accuracy of the determined concentration of the contrast agent in the ROI. Whether the concentration of the contrast agent in the ROI exceeds a preset concentration value may be determined. According to a determination result of whether the concentration of the contrast agent in the ROI exceeds a preset concentration value, a next positioning iteration (e.g., operations 910-930) or a medical procedure (e.g., operation 970) may be performed, which may achieve the dynamic tracking and positioning of the ROI and/or the dynamic monitoring of the concentration of the contrast agent in the ROI, thereby improving the accuracy of the dynamic monitoring of the concentration of the contrast agent in the ROI. The concentration of the contrast agent in the ROI may be plotted on a contrast agent concentration curve and whether the contrast agent concentration curve reaches a preset concentration line may be determined. According to a determination result of whether the contrast agent concentration curve reaches a preset concentration line or the preset concentration value, a next positioning iteration (e.g., operation 910-950) or a medical procedure (e.g., operation 970) may be performed, which may achieve the dynamic tracking and positioning of the ROI, the dynamic monitoring of the concentration of the contrast agent in the ROI, and/or an intuitive display of the process and/or the trend of the change in the concentration of the contrast agent.

It should be noted that the above description regarding the process 900 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 10:
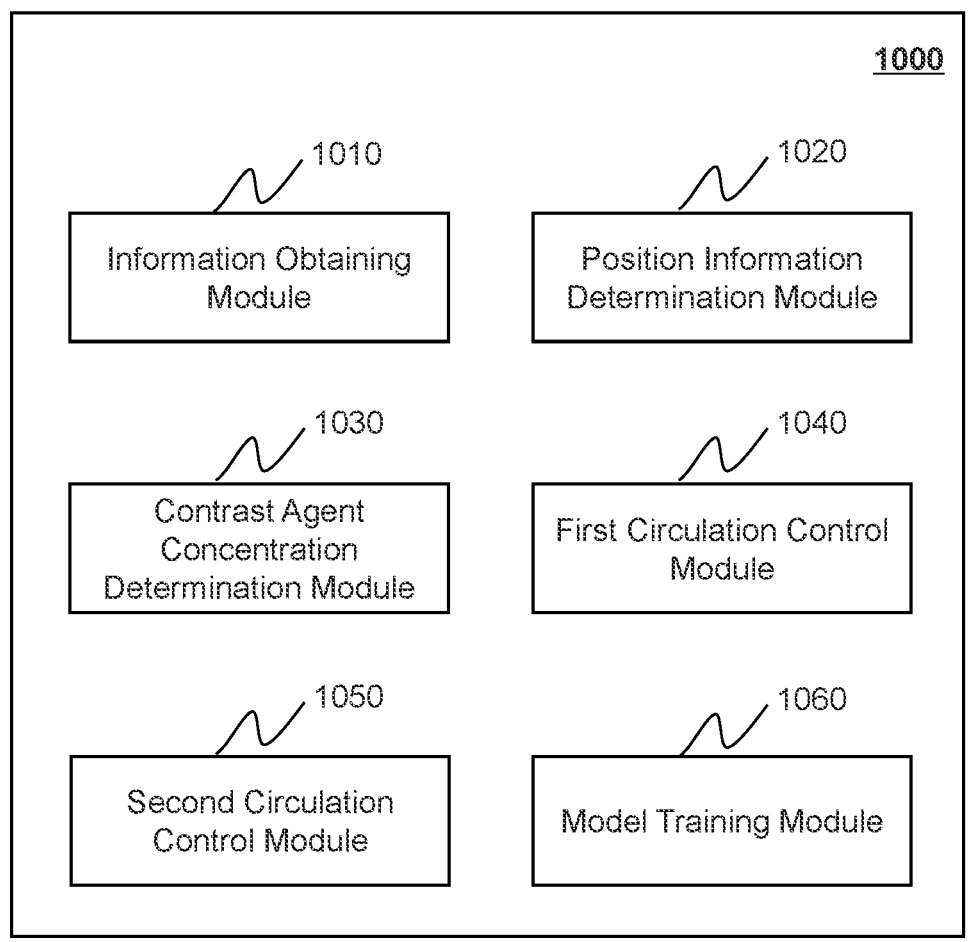
FIG. 10 is a block diagram illustrating an exemplary ROI processing device according to some embodiments of the present disclosure.

FIG. 10 is a block diagram illustrating an exemplary ROI processing device according to some embodiments of the present disclosure. The ROI processing device 1000 may be implemented on the computing device 200 (e.g., the processor 210) illustrated in FIG. 2 or the mobile device 300 illustrated in FIG. 3. The processing device 120 may include an information obtaining module 1010, a position information determination module 1020, a contrast agent concentration determination module 1030, a first circulation control module 1040, a second circulation control module 1050, and a model training module 1060.

The information obtaining module 1010 may be configured to obtain geometric information of an ROI in an image and pixel values of pixels in the image. More descriptions regarding the obtaining of the geometric information of the ROI in the image and the pixel values of pixels in the image may be found elsewhere in the present disclosure. See, e.g., operation 810 in FIG. 8 and relevant descriptions thereof.

The position information determination module 1020 may be configured to determine position information of the ROI in the image based on the geometric information of the ROI and the pixel values of pixels in the image using a positioning model. More descriptions regarding the determination of the position information of the ROI in the image may be found elsewhere in the present disclosure. See, e.g., operation 820 in FIG. 8 and relevant descriptions thereof.

The contrast agent concentration determination module 1030 may be configured to determine a concentration of a contrast agent in the ROI based on the position information of the ROI in the image. More descriptions regarding the determination of the concentration of the contrast agent in the ROI may be found elsewhere in the present disclosure. See, e.g., operation 830 in FIG. 9 and relevant descriptions thereof.

The first circulation control module 1040 may be configured to determine whether the concentration of the contrast agent in the ROI exceeds a preset concentration value. When the concentration of the contrast agent in the ROI exceeds the preset concentration value, that is, the concentration of the contrast agent meets a clinical need, the first circulation control module 1040 may perform a medical procedure on an object associated with the image. When the concentration of the contrast agent in the ROI is less than the preset concentration value, that is, the concentration of the contrast agent does not meet the clinical need, the information obtaining module 1010 may obtain a second image, the position information determination module 1020 may perform ROI positioning operations (e.g., the operations 910-920 illustrated in FIG. 9) based on the second image, and the contrast agent concentration determination module 1030 may perform a concentration determination operation (e.g., the operations 930 illustrated in FIG. 9) based on the second image.

The second circulation control module 1050 may be configured to plot the concentration of the contrast agent in the ROI corresponding to the image on a contrast agent concentration curve. Further, the second circulation control module 1050 may be configured to determine whether the contrast agent concentration curve reaches a preset concentration line or the preset concentration value. When the contrast agent concentration curve reaches the preset concentration line or the preset concentration value, that is, the concentration of the contrast agent meets a clinical need, the second circulation control module 1050 may perform a medical procedure on an object associated with the image. When the contrast agent concentration curve does not reach the preset concentration line or the preset concentration value, that is, the concentration of the contrast agent does not meet the clinical need, the information obtaining module 1010 may obtain a second image, the position information determination module 1020 may perform ROI positioning operations (e.g., the operations 910-920 illustrated in FIG. 9) based on the second image, the contrast agent concentration determination module 1030 may perform a concentration determination operation (e.g., the operations 930 illustrated in FIG. 9) based on the second image, and the second circulation control module 1050 may plot a concentration of the contrast agent in the ROI corresponding to the second image on the contrast agent concentration curve.

The model training module 1060 may be configured to obtain the positioning model by a training process. For example, the model training module 1060 may obtain a plurality of training samples and obtain the positioning model by training a preliminary positioning model based on the plurality of training samples. More descriptions regarding the training process may be found elsewhere in the present disclosure. See, e.g., FIG. 7 and relevant descriptions thereof.

The modules in the processing device 120 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof.

It should be noted that the above description regarding the processing device 120 is merely provided for the purposes of illustration, and not intended to limit the scope of the present disclosure. For persons having ordinary skills in the art, multiple variations and modifications may be made under the teachings of the present disclosure. In some embodiments, two or more of the modules may be combined into a single module, and any one of the modules may be divided into two or more units. In some embodiments, the processing device 120 may include one or more additional modules. In some embodiments, one or more of the units may be omitted. For example, at least one of the contrast agent concentration determination module 1030, the first circulation control module 1040, the second circulation control module 1050, and the model training module 1060 may be omitted. However, those variations and modifications do not depart from the scope of the present disclosure.

In some embodiments, the present disclosure may also provide a storage medium storing computer-executable instructions. The computer-executable instructions may be executed to implement a process (e.g., process 500, process 600, process 700, process 800, process 900) described elsewhere in the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this disclosure are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction performing system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure; it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially," For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system for positioning a region of interest (ROI) of an object, comprising:
   at least one storage device including a set of instructions; and
   at least one processor in communication with the at least one storage device, wherein when executing the set of instructions, the at least one processor is directed to perform operations including:
   obtaining an initial image of the object acquired by performing a preliminary scan on the object using an imaging device;
   obtaining geometric information of the ROI in the initial image, the geometric information of the ROI includes a size and a shape of the ROI; and
   obtaining an image of the object that is acquired by performing, using the imaging device, a tracker scan on the object to monitor a concentration of a contrast agent in the ROI;
   obtaining feature information of the ROI in the object based on the image, the feature information of the ROI including imaging parameter information associated with the ROI, the imaging parameter information corresponding to the concentration of the contrast agent; and
   determining position information of the ROI in the image using a positioning model based on the geometric information of the ROI in the initial image and the feature information of the ROI.

2. The system of claim 1, wherein the obtaining feature information of the ROI in the object includes:
   obtaining marking information of the ROI from the initial image of the object, the marking information including at least one of a size of the ROI, a shape of the ROI, or a position of the ROI in the initial image; and
   obtaining the feature information of the ROI.

3. The system of claim 1, wherein:
   the feature information of the ROI further includes at least one of the size of the ROI, the shape of the ROI, an anatomical feature of the ROI, or pixel information associated with the ROI.

4. The system of claim 1, wherein the imaging parameter information associated with the ROI includes at least one of CT values of the ROI, an average CT value of the ROI, a variance of the CT values of the ROI, or a contrast of the ROI in a subtraction image of the image.

5. The system of claim 3, wherein the at least one processor is directed to perform the operations further including:
   updating the imaging parameter information associated with the ROI based on the position information of the ROI in the image;
   determining whether the updated imaging parameter information associated with the ROI satisfies a condition relating to the concentration of the contrast agent; and
   performing imaging operations based on a determination result of whether the imaging parameter information associated with the ROI satisfies the condition.

6. The system of claim 5, wherein:
   the determination result includes that the updated imaging parameter information associated with the ROI satisfies the condition; and
   the imaging operations include:
   obtaining a second image of the object captured by the imaging device at a second time point subsequent to a first time point when the image is acquired;
   identifying the ROI in the second image using the positioning model based on image information of the second image and feature information of the ROI in the second image; and
   determining whether updated imaging parameter information associated with the ROI in the second image satisfies the condition.

7. The system of claim 5, wherein:
   the determination result includes that the updated imaging parameter information associated with the ROI does not satisfy the condition; and
   the imaging operations include performing a medical procedure on the object.

8. The system of claim 5, wherein the at least one processor is directed to perform operations further including:
   determining a curve indicating a change of the updated imaging parameter information associated with the ROI corresponding to a plurality of images acquired at different time points; and
   transmitting the curve to a terminal device for displaying.

9. The system of claim 1, wherein the determining position information of the ROI in the image using a positioning model based on the geometric information of the ROI in the initial image and the feature information of the ROI includes:
   inputting the geometric information of the ROI in the initial image and the feature information of the ROI into the positioning model; and
   determining the position information of the ROI in the image based on an output of the positioning model.

10. The system of claim 9, wherein the positioning model is obtained by a training process including:
    obtaining a plurality of training samples, each of the plurality of training samples including a sample image, image information of the sample image, an ROI in the sample image, feature information of the ROI in the sample image, and reference position information of the ROI in the sample image; and
    obtaining the positioning model by training a preliminary positioning model based on the plurality of training samples.

11. The system of claim 1, wherein the positioning model includes a machine learning model or a regression model.

12. A method for positioning a region of interest (ROI) of an object, the method being implemented on a computing device including at least one processor and at least one storage device, the method comprising:
    obtaining an initial image of the object acquired by performing a preliminary scan on the object using an imaging device;
    obtaining geometric information of the ROI in the initial image, the geometric information of the ROI including a size and a shape of the ROI;

obtaining an image of the object that is acquired by performing, using the imaging device, a tracker scan on the object to monitor a concentration of a contrast agent in the ROI;

obtaining feature information of the ROI in the object based on the image, the feature information of the ROI including imaging parameter information associated with the ROI, the imaging parameter information corresponding to the concentration of the contrast agent; and determining position information of the ROI in the image using a positioning model based on the geometric information of the ROI in the initial image and the feature information of the ROI.

13. The method of claim 12, wherein the obtaining feature information of the ROI in the object includes:

obtaining marking information of the ROI from the initial image of the object, the marking information including at least one of a size of the ROI, a shape of the ROI, or a position of the ROI in the initial image; and obtaining the feature information of the ROI.

14. The method of claim 12, wherein:

the feature information of the ROI further includes at least one of the size of the ROI, the shape of the ROI, an anatomical feature of the ROI, or pixel information associated with the ROI.

15. The method of claim 12, wherein the imaging parameter information associated with the ROI includes at least one of CT values of the ROI, an average CT value of the ROI, a variance of the CT values of the ROI, or a contrast of the ROI in a subtraction image of the image.

16. The method of claim 14, the method further comprising:

updating the imaging parameter information associated with the ROI based on the determined position information of the ROI in the image;

determining whether the updated imaging parameter information associated with the ROI satisfies a condition relating to the concentration of the contrast agent; and performing imaging operations based on a determination result of whether the imaging parameter information associated with the ROI satisfies the condition.

17. The method of claim 12, wherein the positioning model is obtained by a training process including:

obtaining a plurality of training samples, each of the plurality of training samples including a sample image, image information of the sample image, an ROI in the sample image, feature information of the ROI in the sample image, and reference position information of the ROI in the sample image; and obtaining the positioning model by training a preliminary positioning model based on the plurality of training samples.

18. A non-transitory computer readable medium, comprising executable instructions that, when executed by at least one processor, direct the at least one processor to perform a method, the method comprising:

obtaining an initial image of an object acquired by performing a preliminary scan on the object using an imaging device;

obtaining geometric information of a region of interest (ROI) of the object in the initial image, the geometric information of the ROI including a size and shape of the ROI;

obtaining an image of the object that is acquired by performing, using the imaging device, a tracker scan on the object to monitor a concentration of a contrast agent in the ROI;

obtaining feature information of the ROI in the object based on the image, the feature information of the ROI including imaging parameter information associated with the ROI, the imaging parameter information corresponding to the concentration of the contrast agent; and determining position information of the ROI in the image using a positioning model based on the geometric information of the ROI in the initial image and the feature information of the ROI.

* * * * *